(12) United States Patent
Kung et al.

(10) Patent No.: US 6,508,756 B1
(45) Date of Patent: *Jan. 21, 2003

(54) PASSIVE CARDIAC ASSISTANCE DEVICE

(75) Inventors: Robert T. V. Kung, Auburn, MA (US); David M. Lederman, Marblehead, MA (US); Meir Rosenberg, Newton, MA (US)

(73) Assignee: Abiomed, Inc., Danvers, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/223,645

(22) Filed: Dec. 30, 1998

Related U.S. Application Data

(63) Continuation of application No. 09/023,592, filed on Feb. 13, 1998, now Pat. No. 6,224,540, which is a division of application No. 08/581,051, filed on Dec. 29, 1995, now Pat. No. 5,800,528, which is a continuation-in-part of application No. 08/490,080, filed on Jun. 13, 1995, now Pat. No. 5,713,954.

(51) Int. Cl.$^7$ .................................................. A61F 2/02
(52) U.S. Cl. ........................................................ 600/37
(58) Field of Search .......................... 623/3.1; 600/16, 600/17, 37; 601/153; 607/123, 129

(56) References Cited

U.S. PATENT DOCUMENTS

| | | | |
|---|---|---|---|
| 2,826,193 A | | 3/1958 | Vineberg |
| 3,279,464 A | * | 10/1966 | Kline .......................... 623/3.1 |
| 3,464,322 A | | 9/1969 | Pequignot |
| 3,587,567 A | | 6/1971 | Schiff |
| 3,613,672 A | | 10/1971 | Schiff |
| 4,536,893 A | | 8/1985 | Parravicini |
| 4,628,937 A | | 12/1986 | Hess et al. |
| 4,690,134 A | | 9/1987 | Snyders |
| 4,827,932 A | | 5/1989 | Ideker et al. |
| 4,936,857 A | | 6/1990 | Kulik |
| 4,957,477 A | | 9/1990 | Lundbäck |
| 5,098,369 A | | 3/1992 | Heilman et al. |
| 5,119,804 A | | 6/1992 | Anstadt |
| 5,131,905 A | | 7/1992 | Grooters |
| 5,336,254 A | | 8/1994 | Brennen |
| 5,383,840 A | | 1/1995 | Heilman |
| 5,534,024 A | | 7/1996 | Rogers et al. |
| 5,713,954 A | | 2/1998 | Rosenberg et al. |
| 5,800,528 A | | 9/1998 | Lederman et al. ............. 623/3 |
| 5,902,229 A | | 5/1999 | Tsitlik et al. |
| 5,971,910 A | | 10/1999 | Tsitlik et al. |

FOREIGN PATENT DOCUMENTS

| | | |
|---|---|---|
| EP | 0370931 | 11/1989 |
| FR | 2645739 | 10/1990 |
| GB | 1009457 | 7/1983 |
| GB | 2115287 | 9/1983 |
| GB | 1734767 | 1/1990 |
| JP | 2271829 | 4/1989 |
| WO | 9922784 | 5/1999 |

OTHER PUBLICATIONS

Vaynblat, Mikhail et al., "Cardiac Binding in Experimental Heart Failure" *Circulation*, Supplement I, vol. 92, No. 8 (Oct. 15, 1995), p. I–380.

(List continued on next page.)

*Primary Examiner*—David H. Willse
(74) *Attorney, Agent, or Firm*—Thomas J. Engellenner; Ronald E. Cahill; Nutter McClennen & Fish LLP

(57) ABSTRACT

Artificial implantable active and passive girdles include a heart assist system with an artificial myocardium employing a number of flexible, non-distensible tubes with the walls along their long axes connected in series to form a cuff and a passive girdle is wrapped around a heart muscle which has dilatation of a ventricle to conform to the size and shape of the heart and to constrain the dilatation during diastole. The passive girdle is formed of a material and structure that does not expand away from the heart but may, over an extended period of time be decreased in size as dilatation decreases.

37 Claims, 16 Drawing Sheets

OTHER PUBLICATIONS

Vaynblat, Mikhail et al., "Cardiac Binding in Experimental Heart Failure"*Ann. Thorac. Surg.* 64:81–5 (1997).

Anstadt, G. et al., *A New Instrument for Prolonged Mechanical Cardiac Massage (P)*, Abstracts of the 38$^{TH}$ Scientific Sessions, pp. II43–II44, 1965, Supplement to Circulation, vols. XXXI and XXXII.

Anstadt et al., *Direct Mechanical Ventricular Actuation: A Review,* Elsevier Scientific Publishers Ireland Ltd., Resuscitation, 21 pp. 7–23, 1991.

Anstadt et al., *Pulsatile Reperfusion After Cardiac Arrest Improves,* Ann. Surg., pp. 478–490, October, 1991.

Bencini et al., *'The Pneumomassage' of the Heart*, Surgery, pp. 375–384, Mar., 1956.

Capouva et al., *Girdling Effect of Nonstimulated Cardiomyoplasty,* pp. 867–871, 1993, Ann Thorac Surg.

Carpentier et al., *Dynamic Cardiomyoplasty at Seven Years,* The Journal of Thoracic and Cardiovascular Surgery, pp. 42–54, Jul., 1993, vol. 106, No. 1.

Carpentier et al., *Myocardial Subsitution with a Stimulated Skeletal Muscle: First Successful Clinical Case*, The Lancet, p. 1267, Jun. 1, 1985.

Chekanov, *Nonstimulated Cardiomyoplasty Wrap Attenuated the Degree of Left Ventricular Enlargement*, Ann Thorac Surgery, pp. 1685–1685, 1994, vol. 57.

Kass et al., *Reverse Remodeling from Cariomyoplasty in Human Heart Failure, Circulation*, pp. 2314–2318 May 1, 1995, vol. 91, No. 9.

* cited by examiner

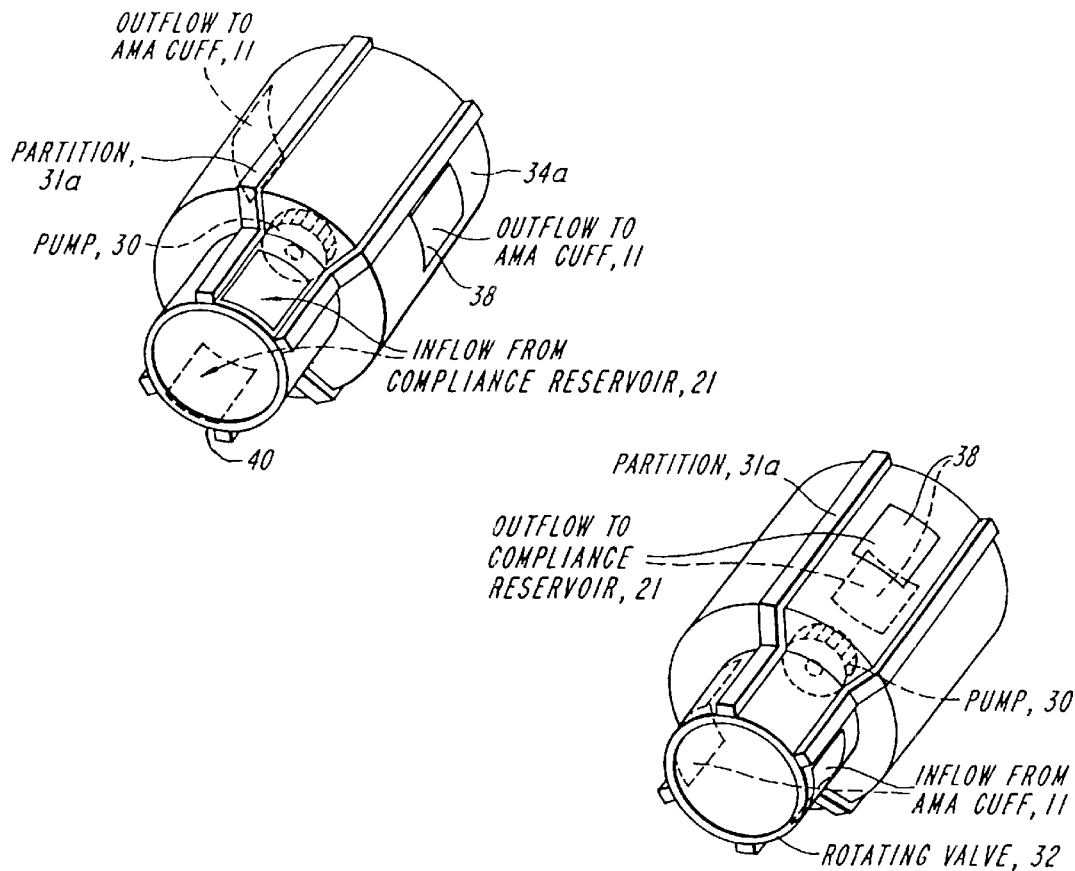
FIG. 11A
FIG. 11B
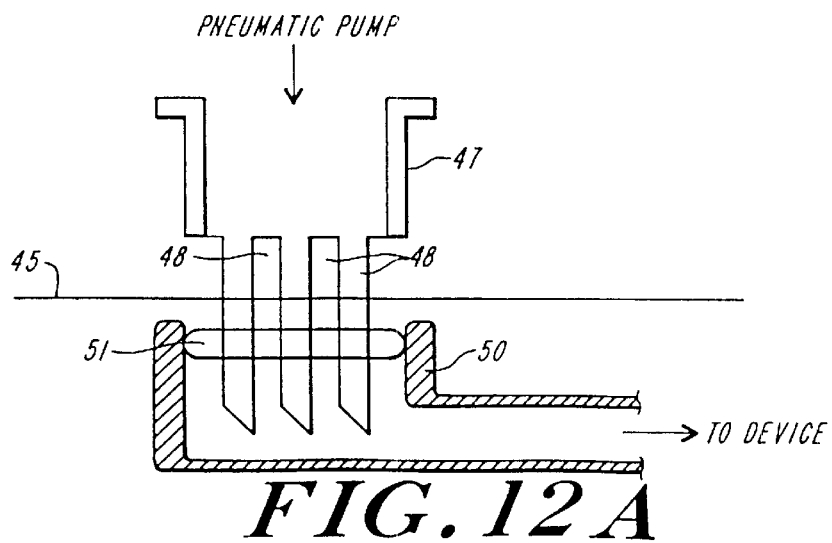
FIG. 12A

PASSIVE CARDIAC ASSISTANCE DEVICE

This application is a continuation of U.S. patent application Ser. No. 09/023,592 filed Feb. 13, 1998, now U.S. Pat. No. 6,224,540, which is a divisional of U.S. patent application Ser. No. 08/581,051 filed Dec. 29, 1995 (now U.S. Pat. No. 5,800,528 issued Sep. 1, 1998), which is a continuation-in-part of U.S. patent application Ser. No. 08/490,080 filed Jun. 13, 1995 (now U.S. Pat. No. 5,713,954 issued Feb. 3, 1998). The contents of each of these patent applications are specifically incorporated herein by reference.

FIELD AND BACKGROUND OF THE INVENTION

The present invention relates to cardiac devices in general, and more specifically to passive and active cardiac girdles.

Patients having a heart condition known as ventricular dilatation are in a clinically dangerous condition when the patients are in an end stage cardiac failure pattern. The ventricular dilatation increases the load on the heart (that is, it increases the oxygen consumption by the heart), while at the same time decreasing cardiac efficiency. A significant fraction of patients in congestive heart failure, including those who are not in immediate danger of death, lead very limited lives. This dilatation condition does not respond to current pharmacological treatment. A small amount, typically less than 10%, of the energy and oxygen consumed by the heart, is used to do mechanical work. Thus the balance, which is the major part of the energy consumed by the heart is used in maintaining the elastic tension of the heart muscles for a period of time. With a given pressure, the elastic tension is directly proportional to the radius of curvature of the heart ventricle. During ventricular dilatation the ventricular radius increases and the energy dissipated by the heart muscle just to maintain this elastic tension during diastole is abnormally increased, thereby increasing oxygen consumption.

A number of methods and devices have been employed to aid the pumping action of failing hearts. Many of these include sacs or wraps placed around the ailing heart, or, in some instances only around the ventricle of the failing heart, with these wraps constructed to provide for active pumping usually, but not always, in synchronism with the ventricular pumping of the natural heart. A number of cardiac assist systems employing a variety of pumping approaches for assisting the pumping action of a failing natural heart have been developed. These systems include those suitable for partial to full support of the natural heart, short term (a few days) to long term (years), continuous pumping to various degrees of pulsability, and blood contacting versus non-blood contacting. Table 1 lists a number of presently developed devices with pertinent operating characteristics.

TABLE 1

| Device | Level of Support | Pulsatility | Duration | Blood Contacting | Comments |
|---|---|---|---|---|---|
| IAPB | Partial <20% | Y | Days to Months | Y | Counterpulsation provides LV unloading |
| Biopump | Full | N | Days | Y | Limited to short duration due to thrombotic potential |

TABLE 1-continued

| Device | Level of Support | Pulsatility | Duration | Blood Contacting | Comments |
|---|---|---|---|---|---|
| Thoratec | Full | Y | Months | Y | Sac-type actuation |
| Novacor | Full | Y | Months | Y | Sac-type pump with electric actuation |
| Hemopump | Partial 50–75% | N | Days | Y | Axial flow pump |
| Heart Mate | Full | Y | Months | Y | Pusher-Plate pneumatic and electric |
| Aortic Patch | Partial | Y | Months | Y | Counterpulsation |
| BVS 5000 | Full | Y | Weeks | Y | Designed for temporary support |
| Anstadt | Full | Y | Days | N | Cardiac resuscitation |
| Cardiomyoplasty | Partial <20% | Y | Years | N | Requires muscle training for active support |

One, more recent development in the field of cardiomyoplasty involves the wrapping and pacing of a skeletal muscle around the heart to aid in the pumping. In that configuration, a pacemaker is implanted to control the timing of the activation of the wrapped around skeletal muscle.

A major consideration in the design of cardiac support systems is the risk of thromboembolism. This risk is most associated with use of artificial blood contacting surfaces. A variety of approaches have been employed to reduce or eliminate this problem. One approach has been the employment of smooth surfaces to eliminate potential sites for thrombi and emboli generation as well as textured surfaces to promote cell growth and stabilization of biologic surfaces. One problem affecting thromboembolism risk in heart assists arises from the use of prosthetic, biologic or mechanical pericardial valves. This risk can be some what lowered by the use of anticoagulation therapy. However, the use requires careful manipulation of the coagulation system to maintain an acceptable balance between bleeding and thromboembolic complications. The textured surface approach employs textured polyurethane surfaces and porcine valves to promote pseudo-intima formation with a stable cellular lining. While thromboembolic rates resulting from these measures are acceptable as temporary measures, improvements, particularly for implantable devices are highly desirable.

A second problem associated with implanted cardiac assist devices Is the problem of infection, particularly where the implanted device has large areas of material in contact with blood and tissue. More recently clinical protocols have improved and even the drive line and vent tubes associated with implants that require some percutaneous attachments have been manageable. However, for a ventricular assist device, quality of life considerations require that vent lines and drive lines which cross the skin barrier be eliminated thereby avoiding the encumbrance to patient activities.

A third problem area in ventricular assist devices is the calcification of these devices. This is particularly so for long term implant situations which may last five years or more. Here again the criticality of this factor is reduced for devices which do not involve direct blood contact.

Another approach employed in ventricular assist has been the development of non-pulsatile pumps. However, once again, the blood is exposed to the surfaces of the pump, particularly the bearing and seal area.

Unlike an entirely artificial heart, in which failure of the system leads to death, a ventricular assist device augments the impaired heart and stoppages should not result in death, unless the heart is in complete failure. However, for most present ventricular assist device systems, stoppage of even a few minutes results in formation of blood clots in the device, rendering any restart of the system a very risky undertaking.

SUMMARY AND OBJECTS OF THE INVENTION

According to one aspect, the present invention an artificial myocardium is constructed of an extremely pliant, non-distensible and thin material which can be wrapped around the ventricles of a natural, but diseased heart. This artificial myocardium mimics the contraction-relaxation characteristics of the natural myocardium and provides sufficient contractility, when actuated, to at least equal the contractility of a healthy natural myocardium. In this arrangement all of the direct blood contact is with the interior surfaces of the natural heart and surrounding blood vessel system. The device is hydraulically actuated in timed relationship to the contractions of the natural heart.

Using this system, the natural heart is left in place and the assist system supplies the reinforcing contractile forces required for satisfactory ventricular ejection.

A key concept for this artificial myocardium system is achieved by the realization of a controllable, artificial myocardium employing a cuff formed of a series of closed tubes connected along their axially extending walls. With sufficient hardware to hydraulically (or pneumatically) inflate and deflate these tubes, a controlled contraction is produced as a result of the geometric relationship between the length of these series of tubes in deflated condition and the length of the series of tubes when they are fluidically filled in the inflated condition. If the cuff is formed of a series of "n" tubes, each of diameter "d" when inflated, connected in series, the total perimeter length of this cuff when deflated is given by $n(\pi d/2)$. However, when these tubes are filled with fluid, they have a circular cross-section such that the length of the cuff is the sum of the diameters in the individual tubes or nd. Thus the ratio of the change in perimeter length between the collapsed and the filled state is $\pi/2$. If this cuff is wrapped around the natural heart, it will, when pressurized, shorten and squeeze the heart by producing a "diastolic" to "systolic" length change of 36%. Typical sarcomere length changes are approximately 20%.

Suitable hardware, including a hydraulic pump, a compliant reservoir and rotary mechanical valve, together with appropriate actuating electronics can all be implanted in the patient's body. If the power source is an internal battery, then power may be transcutaneously transmitted into the body to recharge this battery.

Ventricular dilatation is a clinically dangerous condition for end stage cardiac failure patients. The output of the heart is effected by: (a) end-diastolic volume (ventricular volume at the end of the filling- phase), (b) end-systolic volume (ventricular volume at the end of the ejection phase), and (c) heart rate. When (a) is very large, (b) also tends to be larger and (c) tends to be larger than normal. All three of these factors contribute to large increases in the tension-time integral and therefore to increased oxygen consumption.

Only a small amount of the energy consumed by the heart is used to do mechanical work. For example, with a cardiac output of 5 liters/minute, and $\Delta p$ of 100 mm(Hg), the mechanical work done by the left ventricle is about 1.1 watts, and that of the right ventricle is about 0.2 watts. This compares with the typical total energy consumed by the heart (mechanical work during systole plus the energy cost in maintaining elastic tension during diastole) of about 12 to 15 watts.

Thus, since cardiac efficiency (typically between 3% and 15%) is defined as the ratio of the mechanical work done by the heart to the total energy (or load of the heart muscle): then, Cardiac Efficiency, $$\eta = \frac{\int P_v dV}{\int P dV + k \int T dr}$$

where
 $P_v$: Ventricle Pressure
 P: Pressure
 V: Volume
 T: Tension
 t: Time
 The constant k accounts for conversion of units.

An increase in mechanical work by a large factor results in a small increase in oxygen consumption but an increase in tension time causes a large increase in oxygen consumption. Patients with dilated ventricles who have undergone active cardiomyoplasty have not been reported to show any objectively measurable hemodynamic improvement.

According to a further aspect of the present invention, a completely: passive girdle is wrapped around the ventricle or the entire heart muscle, and sized so that: it constrains the dilatation during diastole and does not effect the action of the ventricle during: systole. With the present surgical techniques, it is expected initial access to the heart to place the girdle in position, will require opening the chest. However, it may be possible to locate a girdle in position without thoracotomy. In one embodiment, a synthetic girdle made from material that can limit tension, but is otherwise deformable to conform to the anatomical geometry of the recipient heart is used. This girdle may be adjustable in size and shape over an extended period of time in order to gradually decrease the ventricular dilatation. A second embodiment employs a fluid filled passive wrap constructed of a series of horizontal sections. This provides for a variable volume to be enclosed by the wrap with volume control being obtained by controlling the volume of fluid from an implantable reservoir within the body. In its most preferable form, this passive wrap can be formed of a series of horizontal tubular segments each individually sealed and attached to one another along the long axis of the cylinder. If the cylinders are made of indistensible material, then changing the volume of fluid from the cylinders being in a substantially deflated condition to one where they are partially or fully inflated, decreases the internal perimeter of the wrap or girdle, thereby decreasing the effective radius of the girdle around the heart. Another feature of the invention is a feedback system, wherein sensors, for example, strain gauges, can be built into an indistensible lining to measure its tension and thereby provide automatic feedback to a hydraulic circuit controlling the wrap volume.

To avoid the problem of potential irritability and damage to the external myocardium cells by virtue of the artificial wrap and its long term constraining contact with the myocardium, one embodiment of the invention employs a tissue engineered lining to protect the myocardium. This tissue engineered lining consists of a polymer scaffold seeded with myocardial cells harvested from the patient's own myocardium using tissue engineering technology. That lining then generates a biological myocardio-interfacing surface and remains firmly attached to the polymer interfacing with the surface from which the wrap is made. Such a lining would integrate biologically to the heart's myocardial cells in a manner analogous to other devices currently being investigated which use cell scaffolds for in vitro and in vitro tissue engineering.

It is therefore an object of the present invention to produce a ventricular assist device system employing an artificial myocardium placed around the natural heart (extra cardiac assist). This design, then, does not contact the bloodstream eliminating many of the problems discussed above.

It is another object of this invention to provide a ventricular assist device which mimics the action of the natural heart while avoiding the compressive action of the direct mechanical ventricular actuation systems on the epicardium.

It is a further object of this invention to provide an artificial myocardium in which the external fluid being pumped is a fraction of the blood volume pumped by the action of the artificial myocardium.

It is yet another object of this invention to provide a ventricular assist device which is compact, requires relatively low energy input and does not require percutaneous components.

It is a further object of this invention to provide a passive girdle to be wrapped around a heart suffering from ventricular dilatation to limit this dilatation and thus improve the performance characteristics of the heart.

It is another object of this invention to provide a passive girdle or vest which can, over a period of time, have its diameter decreased to effect some decrease in dilatation of the ventricle.

Other objects will become apparent in accordance with the description of the preferred embodiments below.

BRIEF DESCRIPTION OF THE DRAWING

FIG. 11A is a cross-sectional view of an energy converter and valve structure in one position for use in the artificial myocardium of this invention;

FIG. 11B is a cross sectional view of the same structure as FIG. 11A but with the valving in a different position for pumping from the hydraulic cuff to the hydraulic reservoir;

FIG. 12A is a cross-sectional view across the skin interface of a subdermal port for emergency access and manual pumping;

DESCRIPTION OF PREFERRED EMBODIMENTS

Figure 1A:
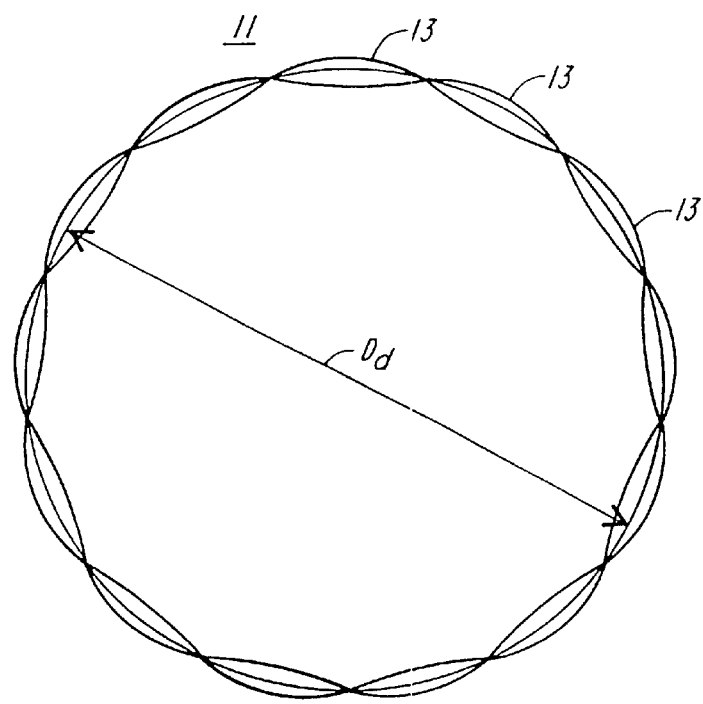
FIGS. 1A and 1B are diagrammatic illustrations of the tube construction of an artificial myocardium in accordance with the principles of this invention.
Figure 1B:
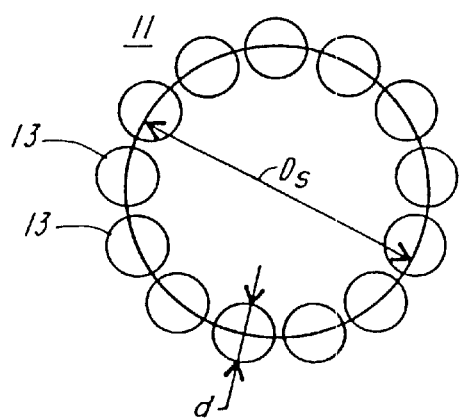

FIG. 1A and FIG. 1B illustrate diagrammatically the operation of the artificial myocardium. The artificial myocardium 11 is formed of a series of tubes planed together in series to form, in this instance a complete circle, which in FIG. 1A has a diameter $D_d$. In FIG. 1B the feature of the tubes is filled hydraulic fluid producing a circular cross-section, shortening the total perimeter of the circular cuff to a circle having a diameter $D_S$. Referring to FIG. 1B, if the diameter of the tube with the circular cross-section is d, then the diameter of the circular cuff is approximately equal to nd/π, where n equals the total number of tubes. On the other hand, when the tubes are no longer filled with hydraulic fluid and are collapsed then the diameter $D_d$ is approximately equal to $$\frac{n(\pi d/2)}{\pi}$$

These expressions follow from the consideration that the series of n tubes in the inflated condition, as illustrated in FIG. 1B form a circle with the number of tubes times diameter of each of the individual tubes. On the other hand in the collapsed condition each one of the tubes has a length equal to its perimeter divided by 2. Since the perimeter is πd then the length of each collapsed tube is πd/2 and the diameter of the cuff in this condition is the sum of the length of the collapsed tubes over π.

When this cuff is placed around a natural heart and the filling and emptying of the tubes is in phase with the systole and diastole of the natural heart, then the shortening of the cuff forces the surrounded ventricle to decrease its diameter thereby causing the ventricle to eject blood. The ejection fraction of this artificial myocardium is. independent of the number of tubes or the heart dimensions. The ejection fraction is a function of only the hydraulic pressure. When the hydraulic pressure is large enough to inflate the tubes to cylinders, the ejection fraction is, $$E_f = \frac{D_d^2 - D_S^2}{(D_d - 2t)^2}$$

where $$D_S \cong \frac{nd}{\pi}, D_d = \frac{nd}{2},$$

t=heart muscle thickness

Figure 2:
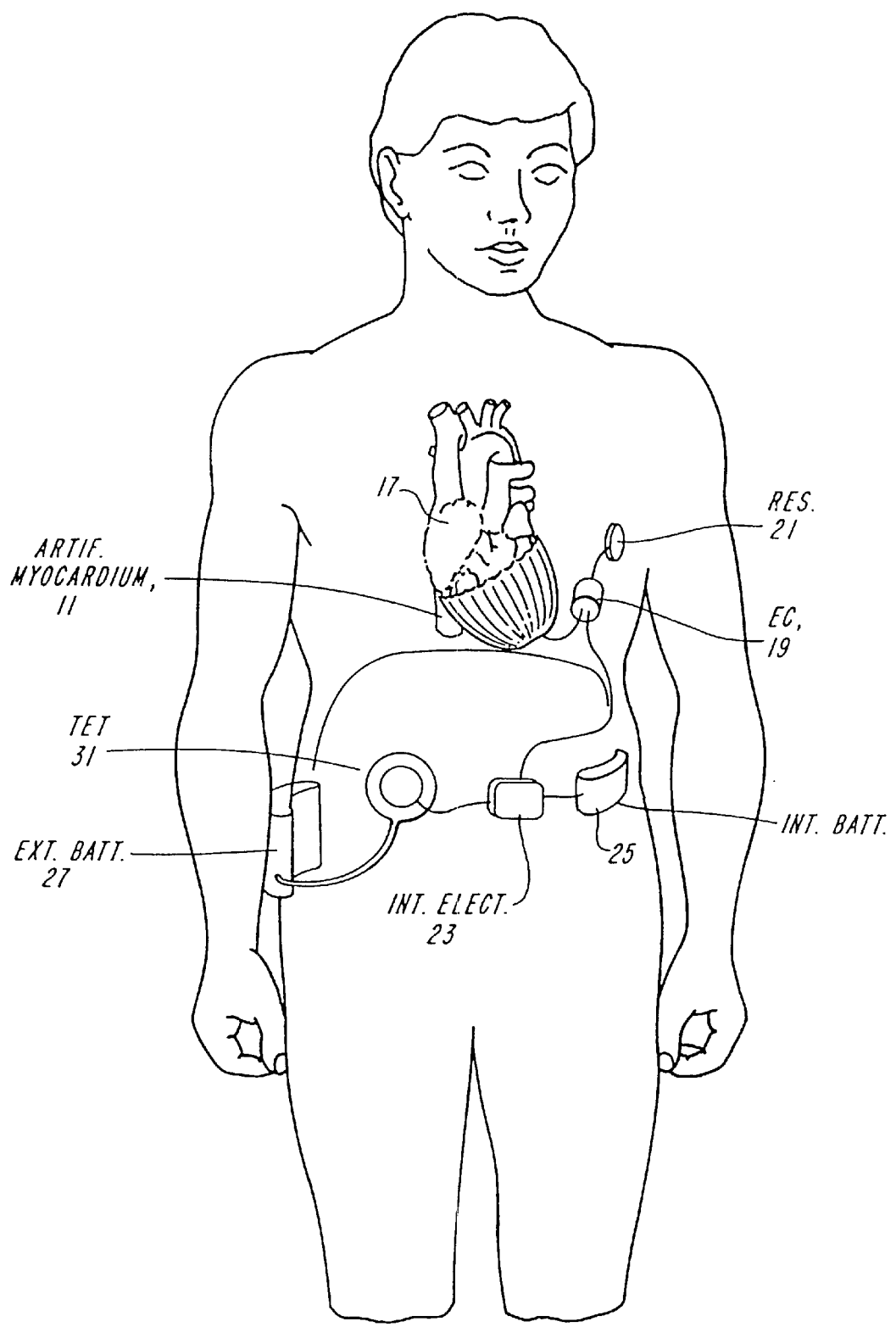
FIG. 2 is a generally diagrammatic illustration of the anatomical placement of the cardiac assist system of this invention in the human body.

FIG. 2 illustrates an artificial myocardial assist system located in the human body. In the illustrated system the artificial myocardium 11 is shown as a cuff placed around the ventricles of the natural heart 17. The hydraulic fluid is pressurized by energy converter 19 either in the direction of the cuff 11 or of a compliant hydraulic reservoir 21. The energy converter 19 is electrically controlled by virtue of internal electric circuit 23 which is powered by an internal battery 25. The internal electrical circuit 23 is also coupled to external battery 27 via a transcutaneous electrical terminal (TET) 31. The energy converter 19 consists of a hydraulic pump coupled to a brushless electric motor to shuttle fluid between the artificial myocardium 11 and the compliant reservoir 21. Flow switching is accomplished by a rotary mechanical valve incorporated into the energy converter, which in turn is synchronized by a control signal generated by detection of the R wave from the ECG signal in the natural heart. Continuous adjustment of the hydraulic pump output allows the level of cardiac assist to be varied on a beat-by-beat basis.

Figure 3A:
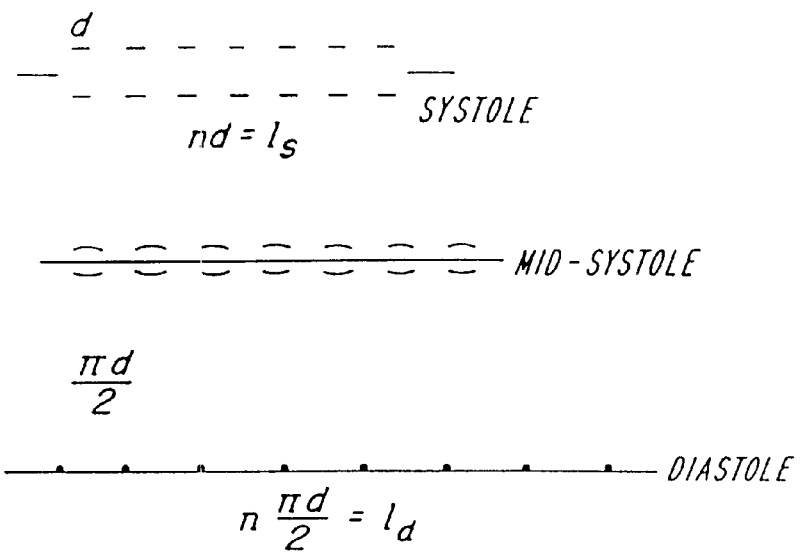
FIG. 3A is an illustration in diagrammatic form of the perimeter length of the artificial cuff at various stages of the natural heart contractions.
Figure 3B:
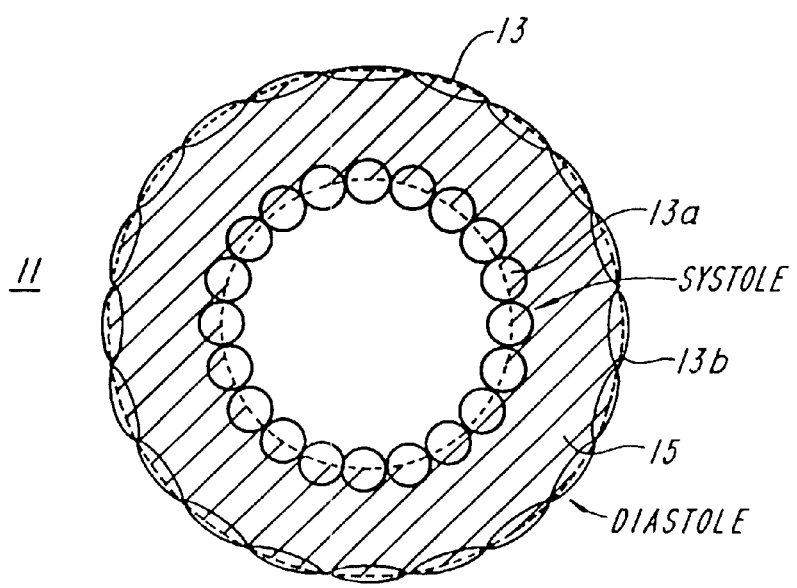
FIG. 3B is an illustration of a cross-sectional view of the systolic and diastolic shapes of the artificial myocardium.

FIG. 3A is a graphical illustration of the length of the perimeter of the artificial myocardium during systole, mid systole and diastole. FIG. 3B is an illustration in cross section view of the systolic and diastolic shapes of the artificial myocardium in a cylindrical geometry. The outer ring illustrates the cylindrical tubes in collapsed form, while the inner ring illustrates those same tubes when they are filled with hydraulic fluid during the systole. The natural heart pumps blood primarily through circumferential contraction. Most of the diastolic to systolic volume change is derived primarily from the 20% change in the circumference component and to a lesser extent the 9% change in the axial length. As can be seen in FIG. 3A and FIG. 3B, the volumetric change of the myocardium is 36% from the relaxed (diastole) position to the fully contracted (systole) position. In the cross-sectional view, and assuming that the artificial myocardium were a completely cylindrical cuff, there is a 60% change in the area between these states in the artificial myocardium, equivalent to a 60% ejection fraction of a healthy heart. Although the description is based on a cylindrical geometry, with interconnecting tapered tubes, the artificial myocardium will match the conical shape of the heart when appropriate taper angle is selected for the tubes.

With this hydraulic design, the natural heart having a typical myocardium thickness, a heart base diameter of 80 mm and an axial ventricular length from apex to base of 50 mm, a left ventricular wrap of the artificial myocardium results in a stroke volume of 83 cc. These values are the same as that which would be expected from a normally operating left ventricle.

One very important factor in the operation of the artificial myocardium is that the hydraulic pressure required for contraction against a given ventricular pressure is directly proportional to the number of tubes n forming this artificial myocardium. From energy conservation principles, the hydraulic flow in this artificial myocardium vanes inversely with the number of tubes. For example, with typical natural heart dimensions, and a hydraulic stroke volume of 24 cc, a pressure of 760 mm Hg produces a left ventricular stroke volume of 95 cc at a mean aortic pressure of 90 mm Hg. Importantly, the hydraulic flows required are much less than the generated blood flow. In this example, the hydraulic flow is approximately 25% of the blood flow produced. These smaller hydraulic flows result in lower hydraulic losses and higher efficiencies. This, taken together with the smaller dimensions for the energy converter and the compliance chamber is very advantageous for an implanted device.

The output of a single energy converter can simultaneously generate different contractile forces for left and right ventricle assist by varying the number of tubes which are wrapped around the left and right ventricles while maintaining an equal drive pressure. If the artificial myocardium on the right side has M times the number of tubes as that on the left side, the contractile pressures on the right side will be M times lower. With this arrangement, the artificial myocardium may be tailored to match differing afterloads from the two ventricles. A good design parameter for considerations for efficiency and tube dynamics would be to operate at a contraction of 22%, which is very close to the contraction value of a natural healthy myocardium. It is believed that with this contraction level, the low mechanical stresses on the artificial myocardium may well result in an operation life of five years, a high reliability for the artificial myocardium.

In the artificial myocardium assist system of this embodiment the contribution from the artificial myocardium is additive to the natural heart with a timing cycle synchronized with the ECG, so that the control algorithm can adjust the hydraulic flow on a beat-by-beat basis to achieve the desired ejection fraction. Thus, if the natural myocardium was completely healthy, minimal pumping would be required by the hydraulic pump. On the other hand, if the natural heart had very little myocardial contractility, then the artificial myocardium would provide almost the entire contracting force.

With this design of the artificial ventricles there is no blood contact with the artificial surfaces of the cardiac assist system, thereby avoiding the principal concerns of the thromboembolism risk. Another important safety consideration, is that if the artificial myocardium system were to stop, the natural forces on the hydraulic fluid will cause it to empty from the artificial myocardium and flow into the compliant reservoir. The only effect of these conditions on the cardiovascular system would be those caused by the collapsed flexible wrap on the myocardium. A subdermal port could be provided to allow emergency actuation of the artificial myocardium with a pneumatic pump placed external to the patient's body. Another consideration is that the control algorithm of the artificial myocardium assist system can be arranged to provide contractions at a fixed predetermined rate if there should be a ventricular fibrillation or tachycardia of the natural heart.

Because the design provides for no contact between the blood and the components of the artificial myocardium assist system, the biocomparability factors are limited to those which relate to the interface between tissues and these components. In this embodiment, the tissue contacting material of the artificial myocardium may be a polyetherurethane, Angioflex®, manufactured by ABIOMED, Inc. of Danvers, Mass.

Figure 4A:
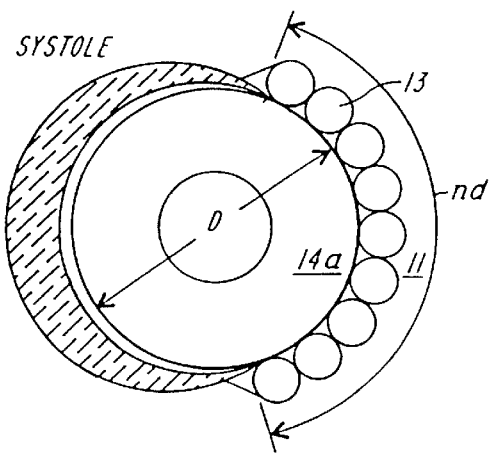
FIG. 4A is a diagrammatic view of a partial wraparound of the left ventricle by the artificial myocardium in the systolic state and FIG. 4B is a diagrammatic view of a partial wraparound of the left ventricle by the artificial myocardium in the diastolic state.
Figure 4B:
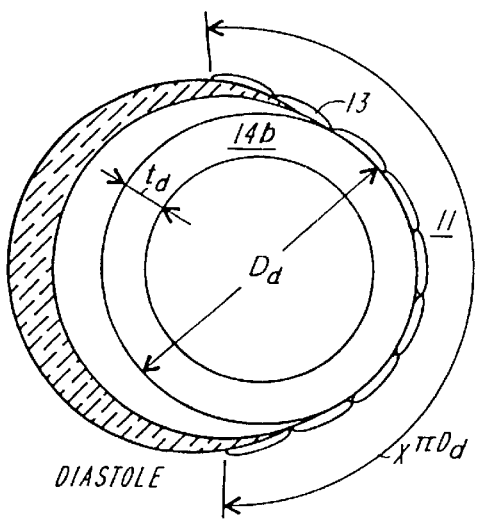

FIGS. 4A and 4B illustrate an example of a partial wrap around the heart for left ventricular support. The full wrap can be used for biventricular support. FIGS. 4A and 4B show the systolic and diastolic positions of the artificial myocardium under this condition. Each of the n tubes are attached at their outer wall to two neighboring tubes except for the two ends. Each tube, when inflated, has a diameter d, resulting in a wrap length of nd. Conversely, when the tubes are deflated the wrap length is $$\frac{n\pi d}{2}$$

Figure 5:
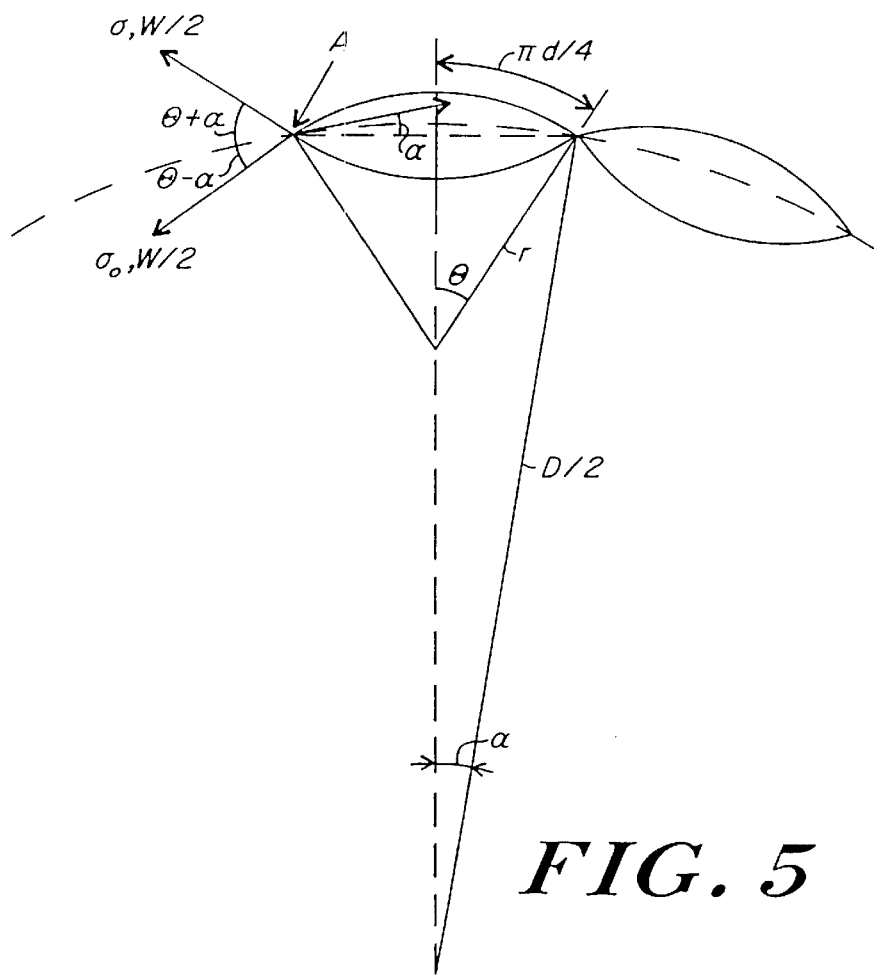
FIG. 5 is a diagrammatic illustration of the geometric relationship of the partially inflated tubes and the encircled heart represented by a radius of D/2.

As illustrated in FIG. 5, when the tubes are partially inflated the length of the wrap is given by $$L = nd \frac{\pi \sin\theta}{2\theta},$$

where θ is the angle representative of the curvature of the wall of the partially inflated tube and is defined as $$\theta = \frac{\pi d}{4r}$$

where r is the radius of the arc of each half of the tube wall when inflated.

Although the ventricle is conical in shape and accordingly the artificial myocardium is conformed to that shape, for simplicity the representation in FIGS. 4A and 4B is of a cylindrical shape. In FIG. 3B the effects of both tube inflation and stroke volume are shown. The systolic contracted shape 13a of the artificial ventricle is plotted concentrically inside the diastolic distended shape 13b. The shaded annulus portion 15 of FIG. 3B represents the stroke volume change due to contraction, while the dotted circle enclosed portion of the inflated tubes represents displacement volume change. For the artificial myocardium this displacement volume has a minor contribution to the stroke volumne.

The volume may be expressed as $$S_V = \frac{\pi}{4} D_d^2 \left[ 1 - \left(1 - \chi + \chi \frac{\sin\theta}{\theta}\right)^2 \right] l + \frac{1}{2} V_H$$

where 1 is the perimeter length of the cuff, where $D_d$ is, as shown, the diastolic diameter of the ventricle and χ is the fraction of the ventricle being wrapped. $V_H$ represents the actual displacement due to the effects of tube inflation in addition to the stroke volume derived from the contraction. If values are substituted in this equation, assuming a typical natural heart diameter of approximately 8 cm, a length approximately 5 cm and a left side partial wrap of χ=½, the contractile change from the uninflated to fully inflated tubes results in a stroke volume of approximately 83 cc. $V_H$ is assumed to be zero. Similarly for a full wrap, the stroke volume would be approximately 150 cc, equivalent to the sum of left and right side stroke volumes.

The ejection fraction achievable using such an assist device may be estimated. The diastolic ventricular volume is given by $$V_d = \frac{\pi}{4}(D_d - 2t_d)^2 l,$$

where $t_d$ is the ventricular wall thickness. Since the ejection fraction is defined as the stroke volume divided by the diastolic ventricular volume, it is given by $$EF = \frac{SV}{\frac{\pi}{4}(D_d - 2t_d)^2 l},$$

Thus, the maximum ejection fraction obtainable for a typical wall thickness of 1 cm and a $D_d$ equal to 8 cm is 59%, a number which is consistent with the ejection fraction for a normal healthy heart.

Figure 6A:
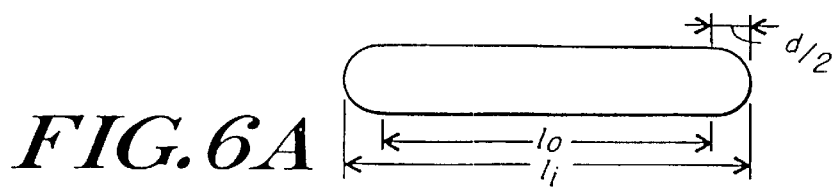
FIGS. 6A, 6B and 6C illustrate factors involved in altering the length of the individual tubes when inflated or deflated, to achieve specific shrink ratios.

FIG. 6A describes a section of a tube having an inflated diameter d and an inflated length 1. The tube ends are formed to hemispheres in the inflated position, the hemisphere radius being d/2.

The following relation can be written:

$$l_i = l_o + d \quad (1)$$

where:
$l_i$ is the inflated length of the tube
$l_o$ is the straight part of the tube
d is the inflated diameter of the tube.

Figure 6B:
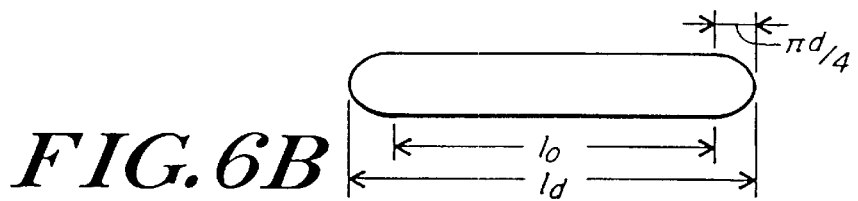

FIG. 6B describes the tube when it is deflated. The flattened diameter of the tube is Bd/2 and its flattened length is:

$$l_d = l_o + Bd/2 \quad (2)$$

where:
$l_d$ is the deflated length of the tube.

The shrink ratio, defined as the change in linear dimensions relative to the original linear dimension $l_d$, is:

$$R = \frac{\left[l_o + \frac{\pi d}{2}\right] - [l_o + d]}{l_o + \frac{\pi d}{2}} = \frac{d\left[\frac{\pi}{2} - 1\right]}{l_o + \frac{\pi d}{2}} = \frac{\pi - 2}{2\frac{l_o}{d} + \pi} \quad (3)$$

where: R=relative change in linear dimensions.

As can be seen from the equation, the ratio R is only a function of the ratio between the diameter d and the length $l_o$. It can also be shown that this ratio does not change if a number of these tubes are connected in series provided $l_o/d$ remains unchanged.

Example: If the required longitudinal shrinkage is 12%, the ratio $l_o/d$ can be calculated, using equation (3) to be:

$$0.12 = \frac{\pi - 2}{\frac{2l_o + \pi}{d}}$$

Figure 6C:

To achieve a contraction of 12% longitudinally, the tube length $l_o$ should be 3.18 times the diameter d. In a particular case, where the tube diameter is 10 mm, the overall tube length will be 41.8 mm. This length is about half of the required length and therefore, two of these tubes will be connected in series to achieve this goal. The series connection can be done by making two wraps of half length, or, making the individual tubes with a shape as described in FIG. 6C.

As discussed earlier the contractile action of the artificial myocardium results from the inflation of the series of tubes that are physically attached to each other. The inflation of these tubes can be accomplished either pneumatically or hydraulically. For a permanently implantable device, the hydraulic approach is more practical. With a pneumatic system, even in the absence of leakage losses, gas permeation across flexing membranes is unavoidable. This effect is not probable in a hydraulic system with a proper choice of working fluids. In addition, the hydraulic system is safer in the event of rupture failure since high pressure cannot be maintained in the event of a leak. In the case of a pneumatic system, a severe leak could result in cardiac compression. In the situation where the artificial myocardium is being employed as an assist device, the natural myocardium can generate some tension, and the artificial myocardium need only generate sufficient tension to boost the intraventricular pressure. Accordingly, the differential pressure, P required of the artificial myocardium may be only 20–30 mm Hg, boosting the ventricular pressure from, for example, 60 to 80–90 mm Hg. The ratio of hydraulic pressure $P_H$ to the load pressure P is expressed by $$\frac{P_H}{P} = \frac{n\tan\theta}{2\pi\cos\alpha} + \frac{1}{2}(1 - \tan\theta\tan\alpha)$$

where $\alpha$ is the half angle subtended by each tube centered to the ventricular axis.

Accordingly, the pump pressure $P_H$ is related to three parameters. First it is directly proportional to load pressure. Thus higher load pressures requires higher drive pressures. Secondly, as the number of tubes, n increases, the drive pressure required for a given boost of intraventricular pressure increases. This is accompanied by a concomitant decrease in the fluid flow of volume per stroke required of the hydraulic pump system. Third, the hydraulic pressure required increases as the tubes are progressively inflated from being fully deflated to fully circular.

Figure 7:
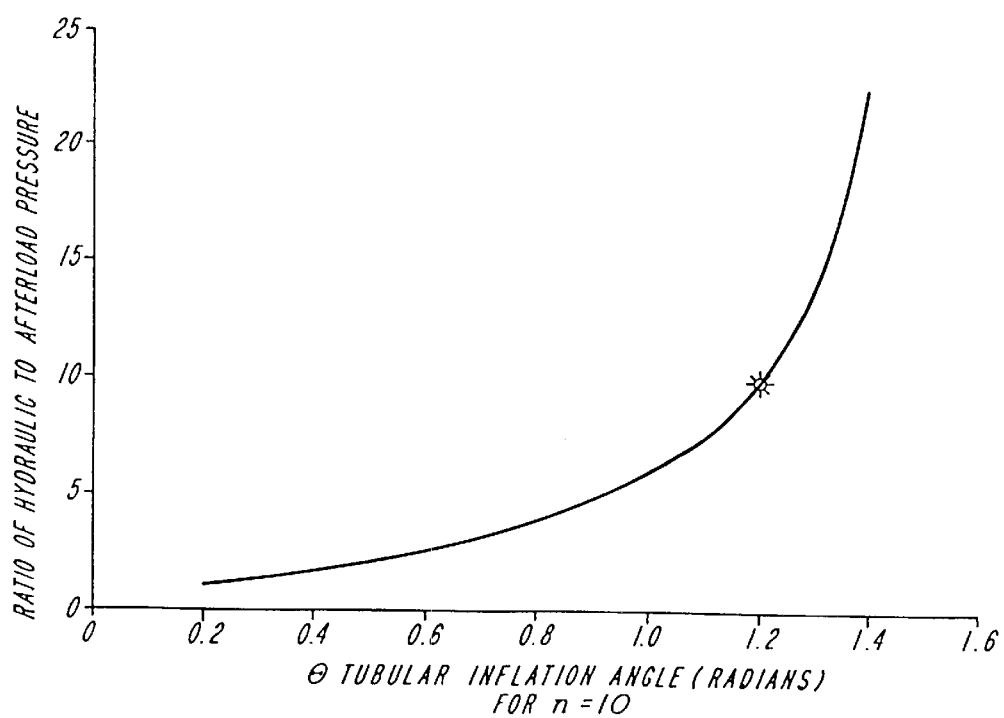
FIG. 7 is a graphical representation of the ratio of hydraulic to afterload pressure as a function of the tube inflation parameter, $\theta$, for n=10.

Illustrated in FIG. 7 is the ratio of the hydraulic to the afterload pressure as a function of the parameter of tube inflation angle 2 for n=10. In the curve of FIG. 7, the targeted operating point is shown by the asterisk. As can be seen a significant contraction is achieved when .theta. is between 1.2 to 1.4 radians, representing a 22% to 30% contraction. Thus, the operational range of the hydraulic pressure is near one atmosphere for full assist against an afterload pressure of approximately 90 mm Hg, and ¼ atmosphere for cardiac boosting, that is, increasing the ventricular pressure by 20 to 30 mm Hg.

As discussed earlier the artificial myocardium requires synchronization of its contraction with the natural heart. Contraction of the device must be timed appropriately with the heart's systole. Additionally, the drive pressures during systolic ejection must be maintained to match the needs of physiologic afterloads.

The first factor, that is, the timing, can be achieved by implanting an epicardial lead in a myocardial region of the natural heart not in contact with the artificial myocardium, which could be near the apical region, or at the right atrial appendage. The artificial myocardium would be timed to contract with the R wave produced on this lead. This detection can employ hardware that is used at the present time in implantable defibrillators. The systolic duration (in milliseconds) is preprogrammed to match its functional dependence to the beat rate (BR) in beats per minute expressed as $\tau_S$=549 msec−2×BR.

Figure 8:
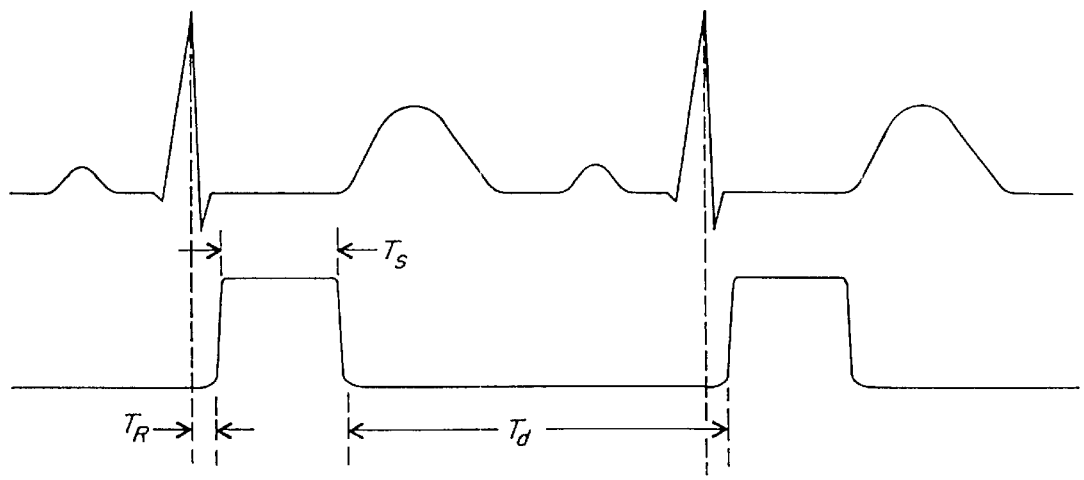
FIG. 8 is a graphical representation of the timing relationship for device actuation.

In FIG. 8 the timing relationship between the ECG and the artificial myocardium is represented graphically. $\tau_R$ is the delay time between the start of the artificial myocardium systole relative to the R wave. $\tau_S$ is the artificial myocardium systolic duration, and $\tau_d$ is its diastolic duration. The exact coincidence of the start of the diastolic duration and the ECG T-wave is not critical. Large deviations from this coincidence could either provide insufficient support ($\tau_d$ starts too early) or hamper diastolic filling ($\tau_d$ starts too late). Of course, irregular rhythms in the natural heart, such as the occurrence of bigeminy, premature ventricular contractions (PVC), or transient arrhythmias can also affect performance of the artificial myocardium system. The most straightforward way of dealing with this situation is to cause the artificial myocardium wrap to be immediately deflated to assume the diastolic state when this occurs. It can also be arranged so that when no ECG trace is detected, the device would contract at beat rates consistent with maintaining physiologic filling pressures. Thus in the extra-cardiac support system of this invention certain unique operating characteristics can be provided when working in conjunction with the natural heart. It can, for example, provide extra contractility not present in other support approaches.

Figure 9:
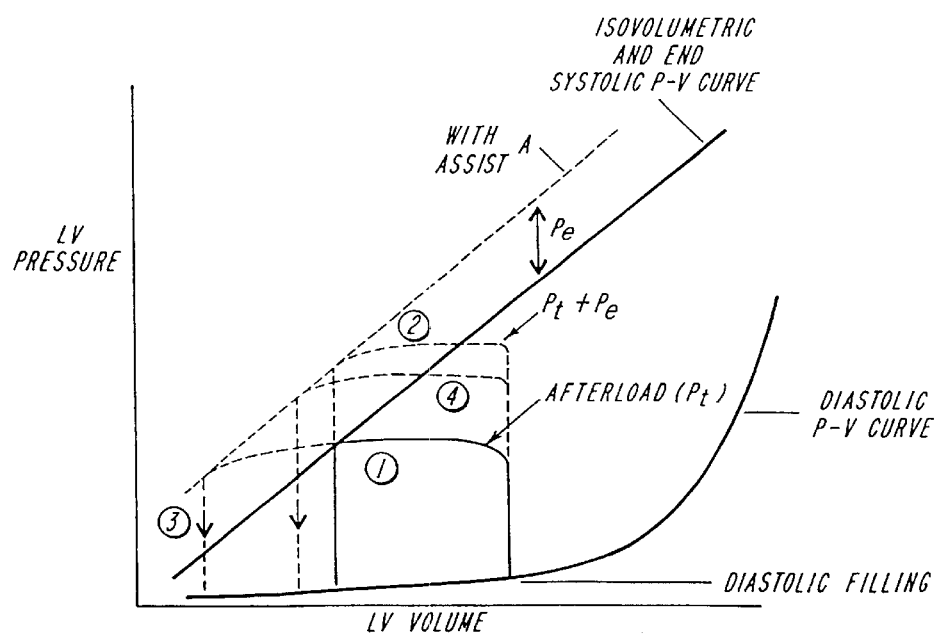
FIG. 9 is a graphical representation of the left ventricular pressure versus the left ventricular volume under various conditions.

FIG. 9 illustrates the left ventricular pressure/volume relationship. In FIG. 9 the left ventricular pressure is plotted against the left ventricular volume. The solid curve (loop 1) illustrates the performance of the natural heart, while the dotted curves show how the pressure volume relationship may be altered in the presence of the extra cardiac assist device. There are two factors that change as a result of the support device: the systolic pressure and the stroke volume. The optimal assist mechanism for this device is to boost the systolic pressure while allowing the myocardium to retain its isovolumetric characteristics by elevating the epicardial pressure ($P_e$) and increasing transmyocardial pressure ($P_t$). The net effect is to displace the isovolumetric curve upwards by $P_e$. This is illustrated by the dashed line, A shown in FIG. 9. Whether the intraventricular pressure ($P_V$) remains at $P_t$, achieves the maximum value of $P_t+P_e$, or more likely reaches somewhere in between the two extremes, depends on the vascular resistance and the ventricular stroke volume. FIG. 9 illustrates the three possibilities. In loop 2, the elevated ventricular pressure is matched by an increase in the afterload. This results in no change in stroke volume. In loop 3, the afterload remains unchanged, while the stroke volume is increased by the assist device. Case 2 would result if the ventricular stroke volume is equal to or greater than that available from the device. This represents, nominally, a healthy heart which requires no assist. The control scheme will be based on achieving a full systolic contraction even though the diastolic ventricular filling may not be complete on a beat by beat basis.

With this control scheme, for a healthy heart which can generate sufficient tension against physiologic afterloads, the contractility required of the artificial myocardium would be zero, and minimal hydraulic power would be required to fill the tubes. This in turn generates minimal epicardial pressures and the assist is at a minimum. However, in cases where the natural heart is not capable of generating normal ejection fractions, the device contraction will extend the stroke volume of the ventricle. In order to realize these higher stroke volumes from the ventricle, the artificial myocardium must provide the additional contractility needed. This requires higher hydraulic power resulting in higher epicardial pressure translating to higher ventricular pressure. Under such circumstances, assist will increase flow and the afterload will also increase as a result of the increased flow. This is illustrated by curve 4, the most likely operating P-V loop under assist conditions.

The control scheme is relatively straightforward. The device will be operating at a full systolic stroke in every beat. Power required to achieve the full stroke will be adjusted on a beat by beat basis. The hydraulic stroke volume will be measured on every beat in order to permit implementation of this algorithm. During diastole, hydraulic pressure will be measured to provide an indication of the end diastolic pressures. This information will be used to determine system beat rate for a heart with no rhythm.

Figure 10:
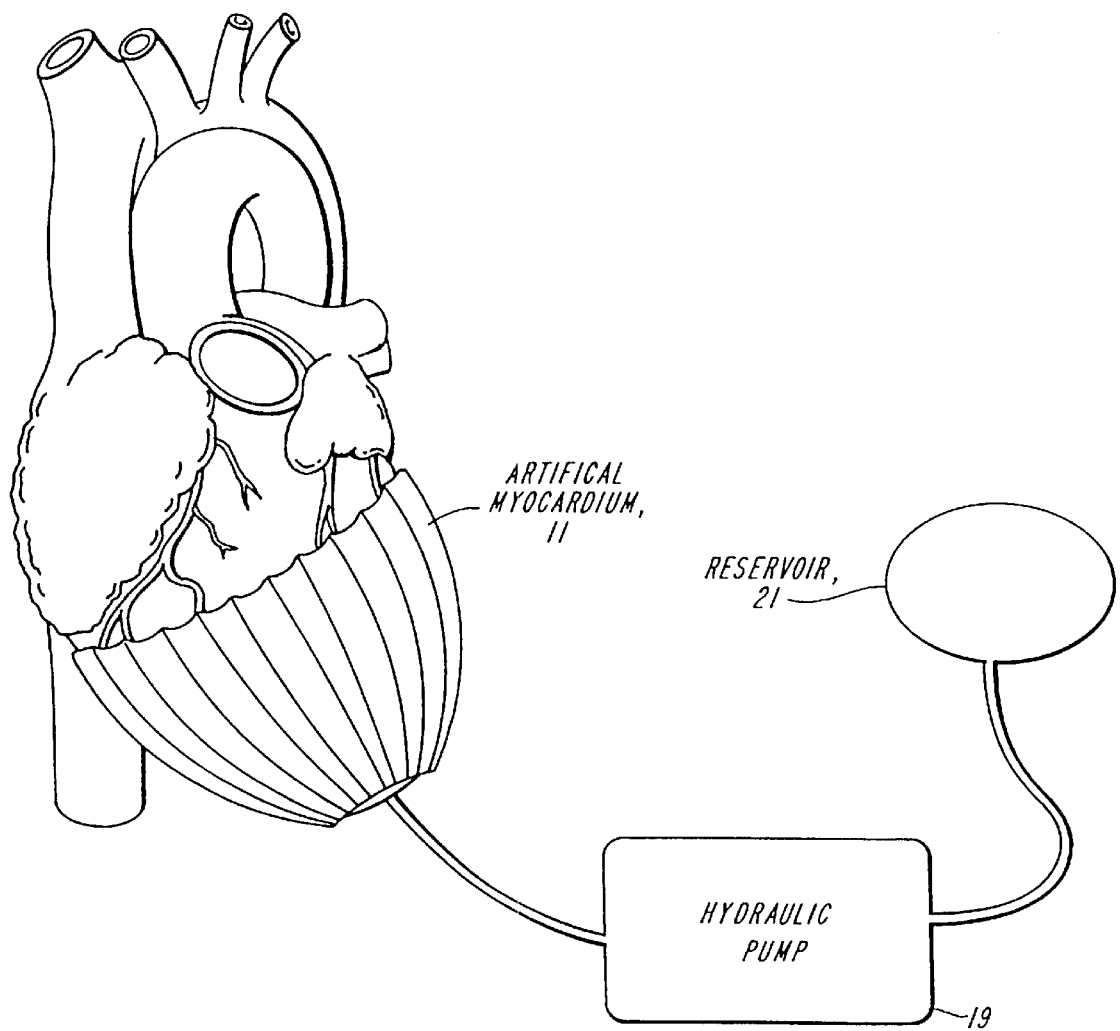
FIG. 10 is a block diagram of the hydraulic system of the artificial myocardium of this invention.

FIG. 10 illustrates in block diagrammatic form the hydraulic system including the artificial myocardium 11, the energy converter 19 and the hydraulic reservoir 21. In one embodiment, the artificial myocardium 11 consists of four layers of polyetherurethane (Angioflex®) reinforced by polyester mesh, fabricated from 40 micrometer fibers. Two layers of the fiber are interwoven to yield tubular interconnections. Separators are inserted in the individual tubes to prevent the opposing inner walls from bonding with each other during the manufacturing process. The process yields a device that has an overall wall thickness of approximately ½ mm and a strength of 150 lbs/in, nearly two orders of magnitude higher than the tensile forces experienced by the device. Attached to the epicardium of the natural heart, the device, when deflated, represents no additional diastolic resistance to the heart. The energy converter 19 shuttles fluid between the flexible reservoir 21 and the artificial myocardium 11. Fluid reversal is achieved by a rotating valve. The system flow resistance is designed to be low such that in the event of a stoppage of the system, fluid in the tubes of the artificial myocardium will automatically empty into the reservoir 21 within a few heart beats. The positive diastolic filling pressure of the natural heart and the negative intrathoracic pressure insures a driving force to empty the fluid from the device. Once it is completely emptied, the artificial myocardium becomes a highly flexible sheet which follows the wall motion of the natural heart without any additional resistance. Such a device can be restarted without any fear of embolic complications after a temporary stoppage.

The direction of hydraulic fluid flow during systole in this cardiac assist device is from the compliant fluid reservoir, through the distributing manifold, and into the individual tubules of the artificial myocardium. During diastole these bladders must be emptied by reversing the direction of hydraulic fluid flow and pumping fluid back into the reservoir. The direction of fluid movement will be reversed by a rotary porting valve in conjunction with unidirectional operation of the centrifugal pump itself.

Unidirectional pump operation has several advantages over reversing the pump direction. Principally, unidirectional rotation of the pump shaft presents much more favorable conditions for bearing life. Although unidirectional pump speed will most likely change between systole (artificial muscle inflation) and diastole, these accelerations and deceleration represents a fraction of those that would be associated with complete reversal of pump direction. Furthermore, in a unidirectional mode, pump impeller design can be optimized for fluid motion in one direction.

Some of the key dimensions and motor performance parameters for a suitable motor for this system are listed below:

overall diameter: OD=1.0 in
overall length: OL=0.5 in
torque constant: KT=0.4 oz-in/amp
voltage constant: $K_B$=0.3 V/kRPM
terminal resistance: $R_M$=0.325 ohms
viscous damping: FI=0.002 oz-in/kRPM The motor performance parameters listed above were used to predict the anticipated torque-speed and efficiency characteristics of the motor. The torque-speed performance characteristics indicate that the specific operating point of 1.2 oz-in at 35000 RPM can be obtained with an applied voltage of 12 V. In this application, the supply voltage will be larger than 12 V, therefore pulse width modulation (PWM) of the motor supply can and will be used to control speed.

Unidirectional pump operation implies that fluid flow reversal will be accomplished using a rotary porting valve. As illustrated in FIGS. 11A and 11B, a balanced inflow and outflow porting configuration is designed to minimize radial loads. The rotary porting valve 32 consists of two concentric sleeves 34a and 34b, a fixed inner sleeve (not shown) and an outer sleeve 34a which can be rotated through a defined angle by a torque motor (not shown). The valve is composed of two pairs of inlet ports leading to the impeller intake, one pair 40 coming from the fluid reservoir and the other pair 38 from the hydraulic cuff 11, and two corresponding pairs of outlet ports off the impeller, one leading to the distributing manifold and one to the fluid reservoir. Accordingly, the valve is designed so that switching the outer sleeve into the systolic position opens the inlet port from the reservoir while closing that from the manifold, and opens the outlet port to the manifold while closing that to the reservoir. Conversely, switching the outer sleeve back reverses the inlet and outlet ports and generates diastole. The rotary porting valve also incorporates hydraulic dampers to prevent valve rebound at the end of switching. FIGS. 11A and 11B illustrate this valving scheme.

The pump motor bearing is a component which requires careful design,considerations By the choice of a unidirectional pump, the major failure mode of bearings due to pump reversals inherent in some designs has been eliminated. However, the artificial myocardium operates at a high RPM in the range of 5,000 to 35,000 RPM. This high RPM places a stringent requirement on the motor bearings.

Bearing load reduction can be achieved by judicious design. Although the outflow pressure is high in the AMA, the surface areas of the energy converter housing exposed to the pressure difference is relatively small, such that the load on the bearings generally remains in the same range. The use of a symmetric paired porting design for the inflow and outflow orifices, allows. the radial loads to be reduced to zero.

For any extra cardiac support device, a volume compensating chamber for the actuating volume is required. Since both the left and right sides are not completely independent of the other, the extra cardiac support cannot alternatively pump the left and the right side. In general, for extra cardiac support, the two sides have to be pumped simultaneously. The artificial myocardium inherently has a volume reduction factor requiring only 25 cc of the hydraulic stroke volume for a biventricular support. This compensating chamber can be directly incorporated on the energy converter as a flexing member or it can be separated from the energy converter via a hydraulic conduit and shaped as a pancake flexible chamber. The latter is the preferred approach since this provides additional flexibility in chamber placement. This chamber would be a 2½ diameter sac with flexible membranes to yield a 1 cm excursion. The body of the chamber can be made from Angioflex®. A velour layer can be the enclosure to provide tissue layer stability.

The control of the proposed artificial device needs to incorporate three key modes. These are, (1) synchronized contraction and dilatation with the heart when a normal R-wave is discerned, (2) no pumping during intermittent arrhythmia, and (3) pumping at rates determined only by filling pressures during fibrillation and cardiac arrest. An additional design criterion is to ensure that the device does not work against the heart. The proposed control algorithm consists of three modes discussed below.

Synchronization is achieved by sensing the rhythm of the natural heart, or paced signals for subjects with implantable pacers. Two basic approaches are available, using either the P-wave or the R-wave, the choice being governed by the conduction capability of the heart.

P-wave may be preferable as the reference for synchronization, since the right atrium remains free from any mechanical contact with the device. Naturally, if a subject suffers from frequent atrial flutter or atrial fibrillation, reliable P-waves would not be available. In addition, AV block would exclude the use of the P-wave. Patients with these pathologic conditions would require R-wave sensing. Epicardial leads can be used for either sensing mode. For atrial sensing, a lead can be sutured to the atrial appendage, while ventricular sensing can be achieved by a corkscrew electrode attached near the apex where no direct squeezing of the myocardium would occur. Bipolar electrode designs may be used in order to localize signal reception especially, P-waves, with reduced noise pick-up in the acquired signals. Unipolar leads can be used for R-wave sensing since this is the simplest type of electrode for ventricular epicardial fixation.

Whether P-wave or R-wave sensing is used, the algorithm is designed for synchronous contraction of the artificial device and the myocardium. For a subject with a regular heart beat, this can be achieved readily. For P-wave sensing, the device systole is timed to initiate after ≈160 msec, a normal AV delay, following P-wave detection. With R-wave detection, device actuation is initiated immediately. An anticipation algorithm which is based on the prior R-R intervals can also be used. Such algorithms are available.

Figure 12B:
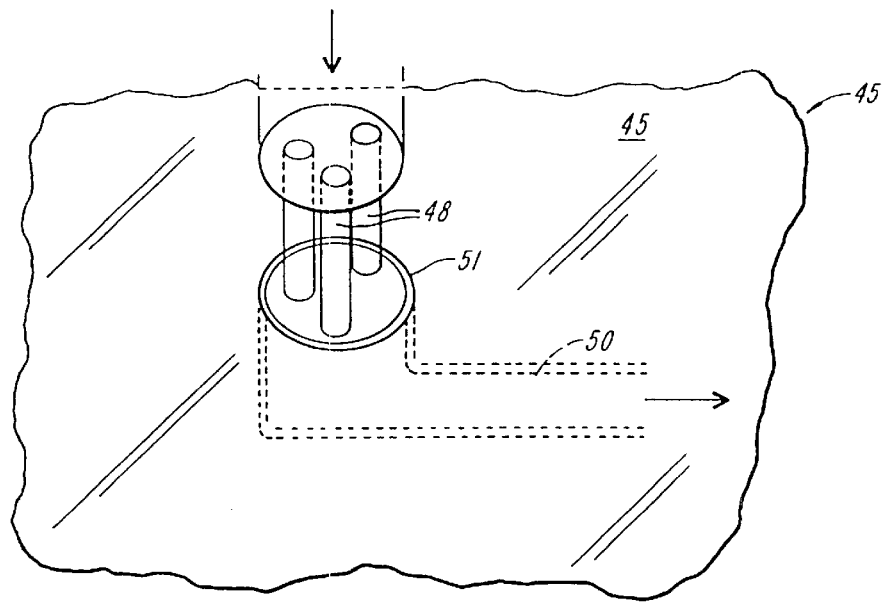
FIG. 12B is an "X-ray" view of the access system of FIG. 12A viewed externally.

In FIGS. 12A and 12B there is illustrated a subdermal port for the artificial myocardium assist system in case there is a failure of the hydraulic pumping capacity. FIG. 12A is a cross sectional view across the skin interface 45 and FIG. 12B is an "x-ray" view of the system viewed externally. In the case of a system failure, as a result of electronic or mechanical problems, the subdermal port can be accessed through a skin puncture with an array 48 of 15 gauge needles. The procedure would involve the extraction of the hydraulic fluid using a 50 cc syringe. This extraction would collapse the artificial myocardium cuff 11. A hand operated pneumatic pump (not shown) could then be connected to the needle manifold 47 to activate the artificial myocardium. The reason for the extraction of the hydraulic fluid and subsequent manual use of a pneumatic pump is that the flow resistance through a i cm long parallel array of 15 gauge (1 mm ID) needles is less than 20 mm Hg for air, while the use of hydraulic fluid would result in pressure losses which are orders of magnitude higher. The artificial myocardium system would be implanted through a median sternotomy. This procedure is sufficiently simple so that it would be possible without bypasses, although severely compromised patients might: require bypass for support during the surgical procedure. Of course, other perhaps less invasive, surgical techniques could possibly be employed for this implantation. An appropriately sized artificial myocardium cuff 11 would be wrapped around the natural heart. The energy converter 19 and the hydraulic reservoir 21 would be implanted in the thorax. It is estimated that the total volume and weight of the thoracic unit would be approximately 105 cc and 165 g respectively. The energy converter and the fluid reservoir, which in practice could be an integral part of the energy converter, would be anchored to the rib cage with a flexible hydraulic connection to the artificial myocardium cuff 11 and an electrical cable tunneled through the costal diaphragmatic region to the electronic components which could be implanted in the abdomen. These implant locations are illustrated in FIG. 2. It is important that the artificial myocardium cuff 11 is anchored properly relative to the natural heart such that during systolic contraction, the heart would not slip out of the myocardium cuff 11. Suitable attachment arrangements are, for example, illustrated in U.S. Pat. No. 4,957,477.

The primary biocompatibility issue for the artificial myocardium relates to the epicardial tissue/cuff interface, or pericardial tissue/cuff interface. The material in contact with the epicardium or the pericardiurn will be the polyetherurethane. material Angioflex®. Other implanted components would consist primarily of cable jackets made from either medical grade room temperature vulcanizing rubber (RTV) or Angioflex® polyurethane. Non-flexing parts would consist of titanium as casing for the energy converter and electronics packages. Infectious risks would be minimized in this design by the elimination of percutaneous exit and entry sites into the body, by quality control of surfaces and by choices of materials in contact with the tissue.

Figure 13:
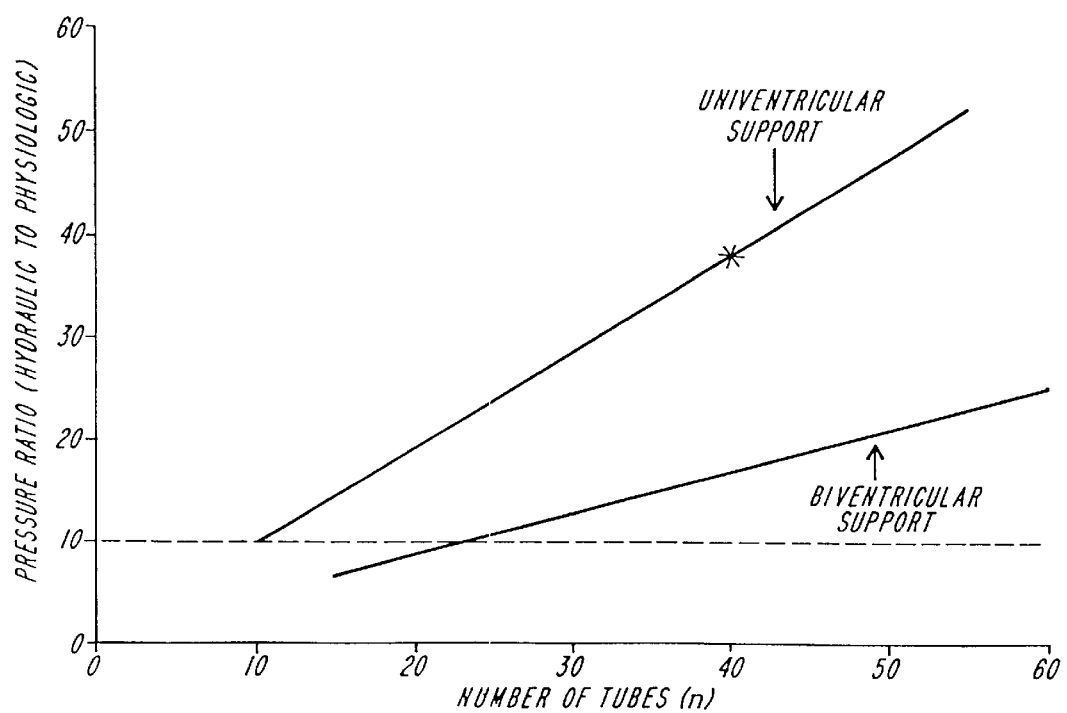
FIG. 13 is a graphical representation of the hydraulic to physiological pressure ratios as a function of the number of tubes for both univentricular and biventricular support.
Figure 14:
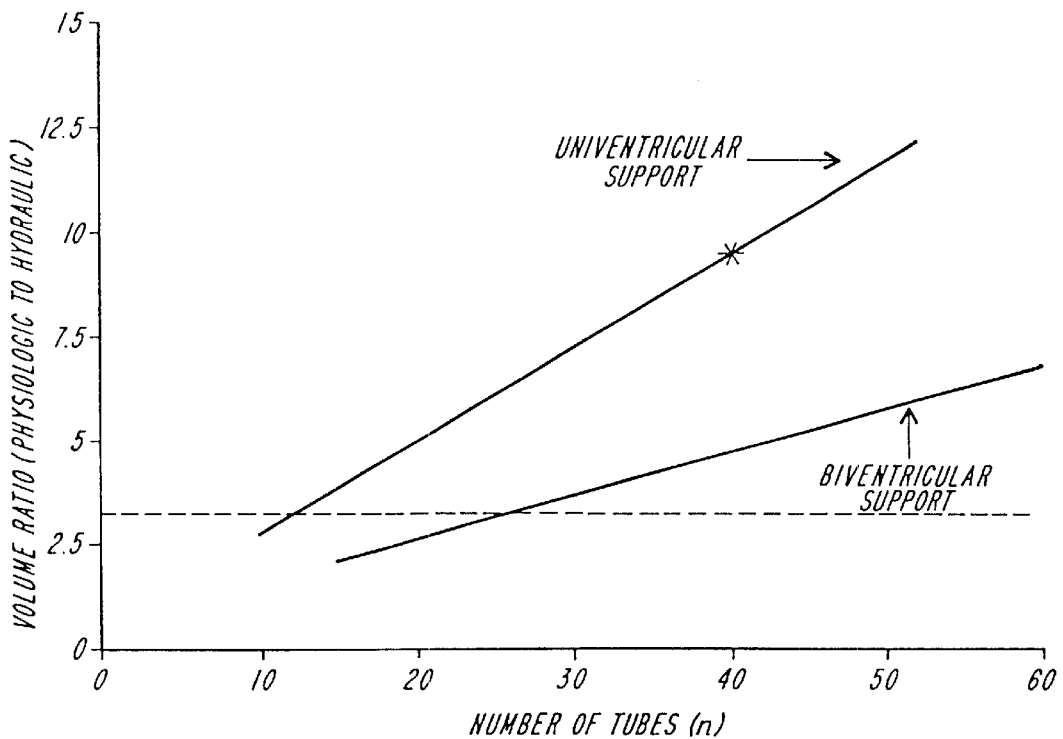
FIG. 14 is a graphical representation of the physiological to hydraulic volume ratios as a function of the number of tubes for both univentricular and biventricular support.
Figure 15:
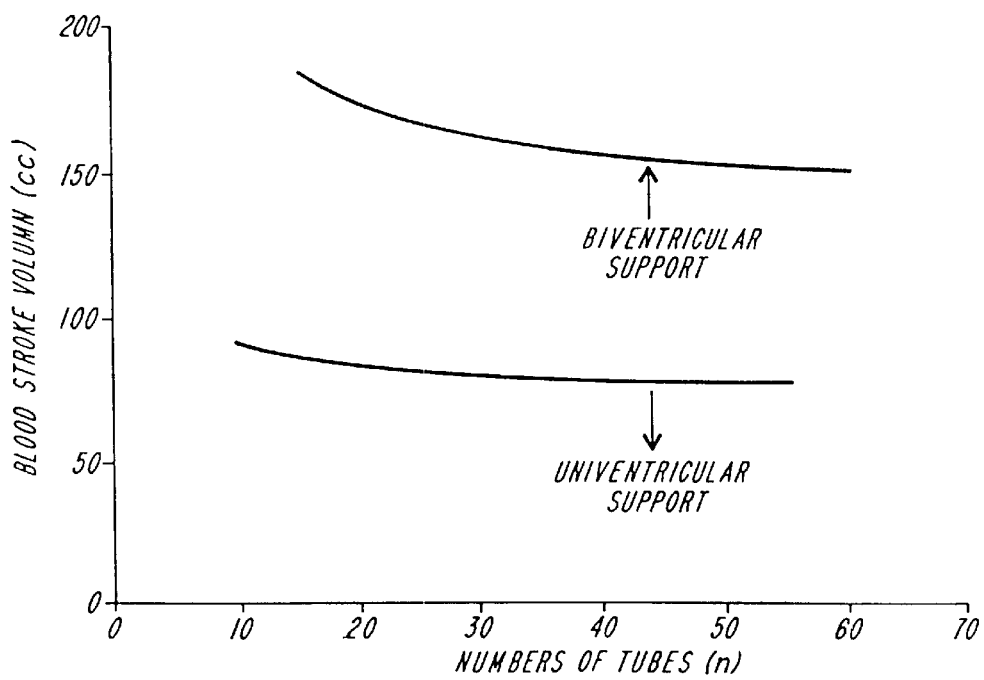
FIG. 15 is a graphical representation of the blood stroke volume as a function of the number of tube segments in the artificial myocardium of this invention.

FIGS. 13 and 14 show the calculated pressure and volume ratios of the hydraulic and physiologic blood system fluids as a function of the number of tubes in the artificial myocardium. FIG. 13 shows the hydraulic physiological pressure ratio as a function of the number of tubes for both biventricular support and univentricular support. FIG. 14 shows the physiological to hydraulic volume ratio. These figures show that as the number of tubular segments increases, the required hydraulic stroke volume decreases while the required hydraulic pressure increases. For a volume ratio of three, the univentricular support (½ of the total wrap) would require 11 segments, while the biventricular support would need 23 segments because of the larger perimeter for biventricular support. This volume amplification between the hydraulic stroke volume and the blood stroke volume is very significant, since it permits the actuating system for the artificial myocardium to be small and compact in size. In order to take advantage of this volume amplification, the pressure required to inflate the tubes to the appropriate extent for a significant stroke work is approximately 10 times the afterload pressure of the blood being pumped. In the figures, the intersections of the univentricular and biventricular supports with the dashed horizontal line indicate these operating points. FIG. 15 illustrates the blood stroke volume in cc's as a function of the number of tube segments (n) in the artificial myocardium. As illustrated, the stroke volume does not have a strong dependence on n, especially when n becomes large and the hydraulic displacement component becomes negligible compared with the contractile effect. For a completely failed ventricle, in order to generate 100 mm Hg of systolic pressure, the hydraulic drive pressure required will be approximately 1,000 mm Hg. This value is illustrated by the star shown in FIG. 7. The benefits derived from operating the energy converter 19 at lower flow and higher pressures are higher system efficiency as a result of lower flow losses and smaller system size due to the lower volume requirement. The gain in the hydraulic efficiency will be primarily in the energy converter 19. For artificial myocardium cuff 11, the flow velocities in the individual tubes is independent of the number of tubes. The volume of each tube scales with the area of the tube so that the flow velocity is a parameter determined only by physiologic requirements. For a 65 cc stroke volume at a beat rate of 140, the peak hydraulic flow velocity in the tubes is approximately 15 cm per second, resulting in a dynamic pressure of approximately 0.1 mm Hg, which has no impact on efficiency when compared to driving pressures on the order of one atmosphere. With this design, the wall stresses in the artificial myocardium cuff 11 are, as in flow losses, independent of the number of tubes used in the wrap. The wall stresses in the walls connecting the tubes are only functions of the physiological parameters, such as the heart diameter and the physiological pressure. The wall stress is given as the product of the hydraulic pressure $P_H$ and the tube radius, r, and is a constant, independent of the number of tubes, n.

The design consideration for the number of tubes per wrap will be determined by practical considerations such as the fabrication techniques and energy converter efficiency.

Figure 16:
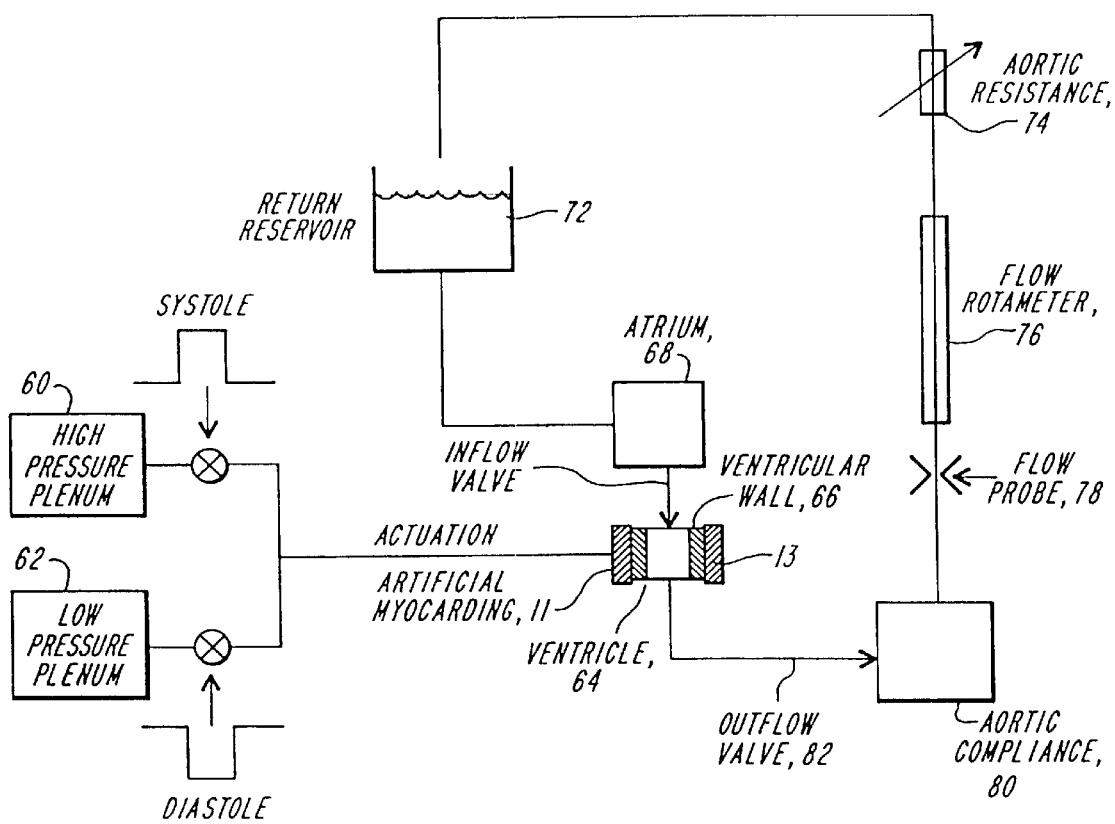
FIG. 16 is a diagrammatic illustration of a mock loop used for in vitro tests.
Figure 17:
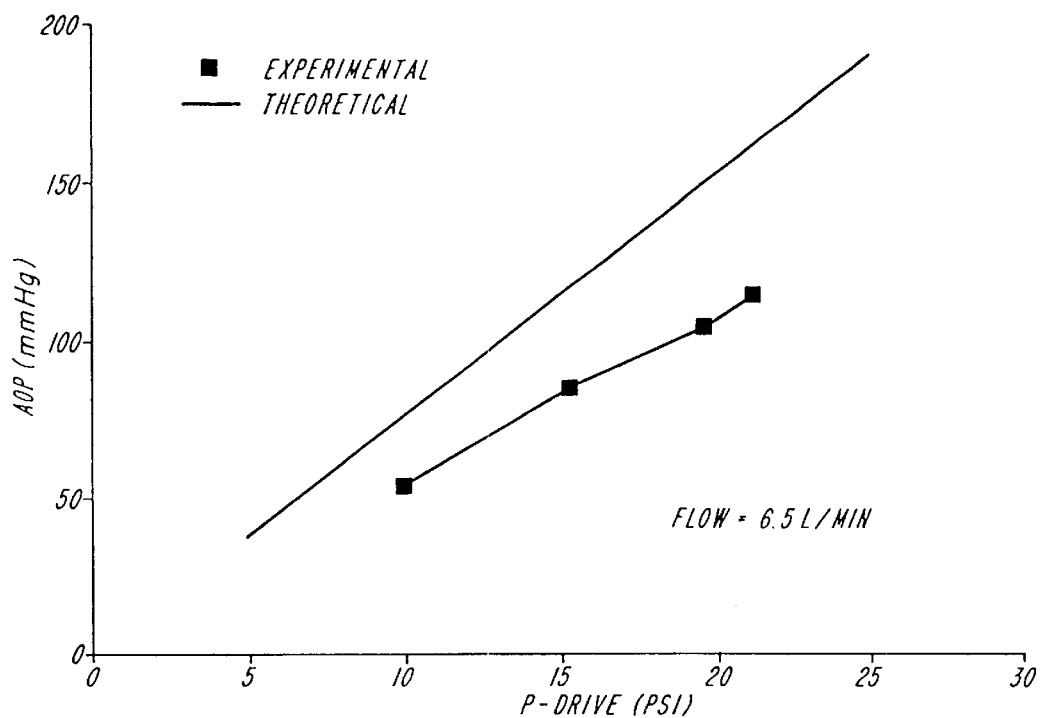
FIG. 17 is a graphical representation of the relationship between Afterload Pressure (AOP) and Driving Pressures (P-Drive) for the artificial myocardium.

FIG. 16 shows a mock loop used for in vitro tests of the artificial myocardium. Fluid from the reservoir 72 enters an atrium 68 which empties through a inflow valve 70 to the ventricle 64. The ventricle consists of a cylindrical bladder which is surrounded by another concentric cylindrical pouch. A space between the bladder and the pouch is filled with a viscous fluid to simulate the ventricular wall. The exterior of the pouch has fitted eyelets spaced to accept an artificial myocardium simulating a left ventricular wrap. The outflow from the artificial ventricle 64 is coupled through another tri-leaflet valve 82 to an aortic compliance chamber 80, followed by a flow probe 78 and a flow rotameter 76. The outflow resistance 74 is adjustable. The return flow empties into the reservoir 72. For this study the artificial myocardium assist system was actuated using a pneumatic drive console consisting of a high pressure plenum and a low pressure plenum which were alternately switched to the device by solenoid valves initiating systole and diastole respectively. This drive mechanism replaces the hydraulic energy converter which would be employed in the implantable system. For this study FIG. 17 illustrates a linear relationship between the afterload pressure (AOP) and driving pressures for the artificial myocardium. The theoretical calculated value is shown as the solid curve, while the square dots indicate the values determined in this experimental study. The flow output was maintained constant by adjusting the aortic resistance. In the illustrated set of measurements the flow was maintained at 6.5 liters per minute, with a filling pressure of 14.6 mm of mercury, a beat rate of 169 beats per minute and a systolic duration and duty factor of 168 milliseconds and 40% respectively. The device used in this study had 7 adjacent tubes and provided 50% wrapping of the pouch simulating the natural heart ventricle. The diameter and length of the pouch were 6 cm and 5 cm respectively, fairly typical of a small, left ventricle. Based on calculations, the anticipated stroke volume was 46.7 cc and the measured stroke volume was 38 cc, 82% of the theoretical value.

Figure 18:
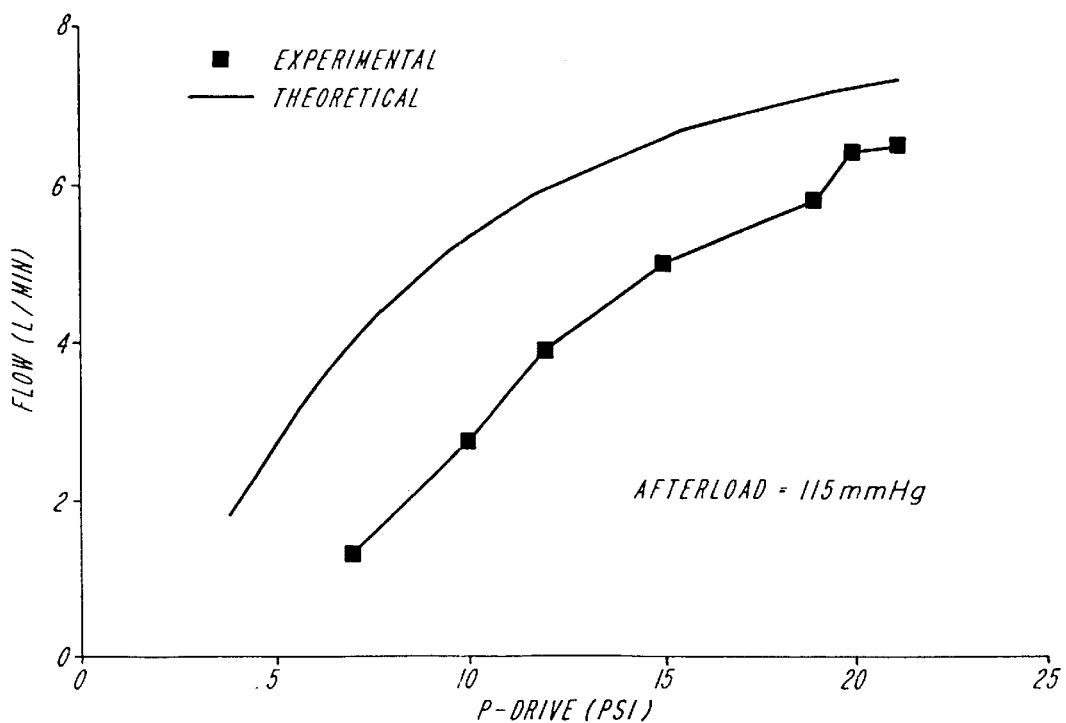
FIG. 18 is a graphical representation of flow sensitivity to drive pressure at constant afterload pressure.

A second set of measurements was obtained in this study by maintaining a constant afterload, while the drive pressure was varied and the resultant ventricular flow recorded. The results of this study are illustrated in FIG. 18. The solid curve shows the calculated values and the set of square points illustrate the measured values. The conditions were similar to those for the experiment illustrated in FIG. 17. FIG. 18 also illustrates the calculated flow versus the drive pressure relationship. The outflow pressure was set at 115 mm Hg, which is the intercept of. the drive pressure at zero flow. This study showed that the experimental pneumatic drive pressure was slightly higher than that which would have been predicted by the theoretical calculation. The data from this study indicates by controlling the drive pressure, which is equivalent to adjusting the contractility of the artificial myocardium, both flow and pressures can be enhanced.

Figure 19A:
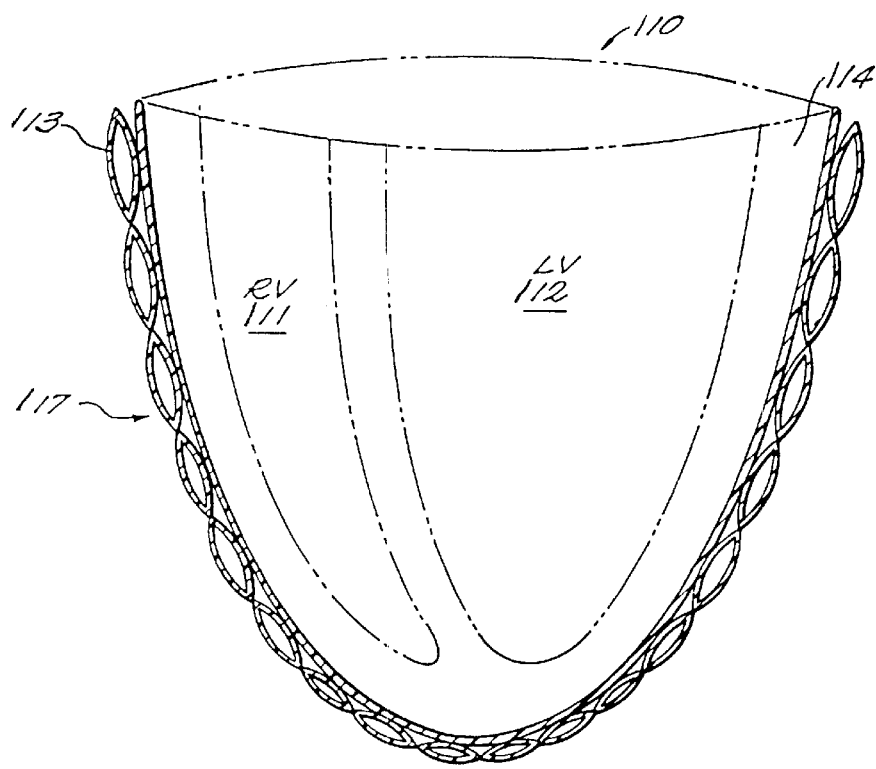
FIG. 19A is an illustration generally in cross sectional form of a heart girdle constructed in accordance with the principles of this invention.
Figure 19B:
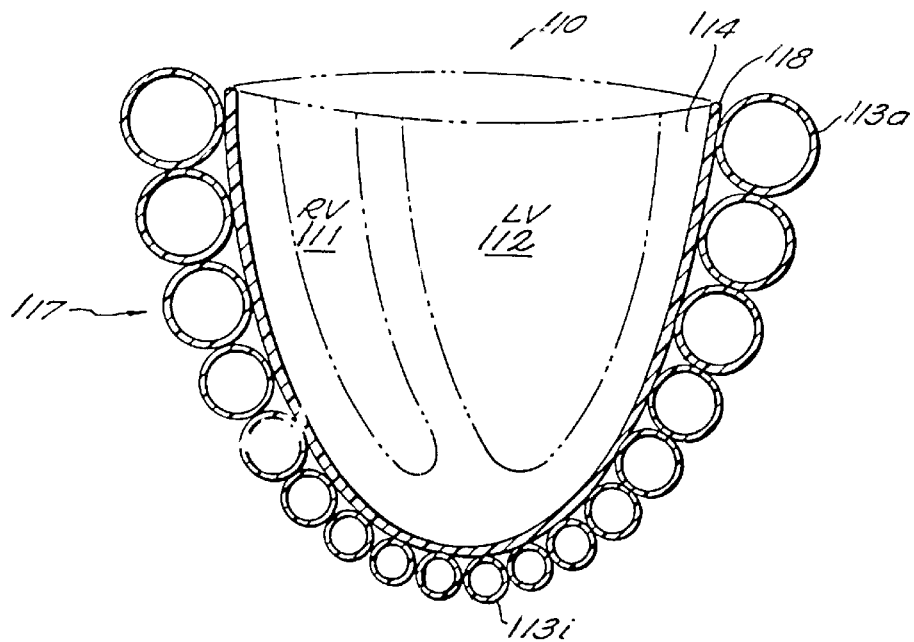
FIG. 19B is an illustration in cross-sectional form of the heart girdle of FIG. 19A with the girdle in a pneumatically filled condition.

In FIGS. 19A and 19B there is illustrated one embodiment of a girdle for wrapping around a heart to constrain dilatation of the ventricle and limit the amount of energy and oxygen required to maintain the heart muscle in tension.

Figure 20:
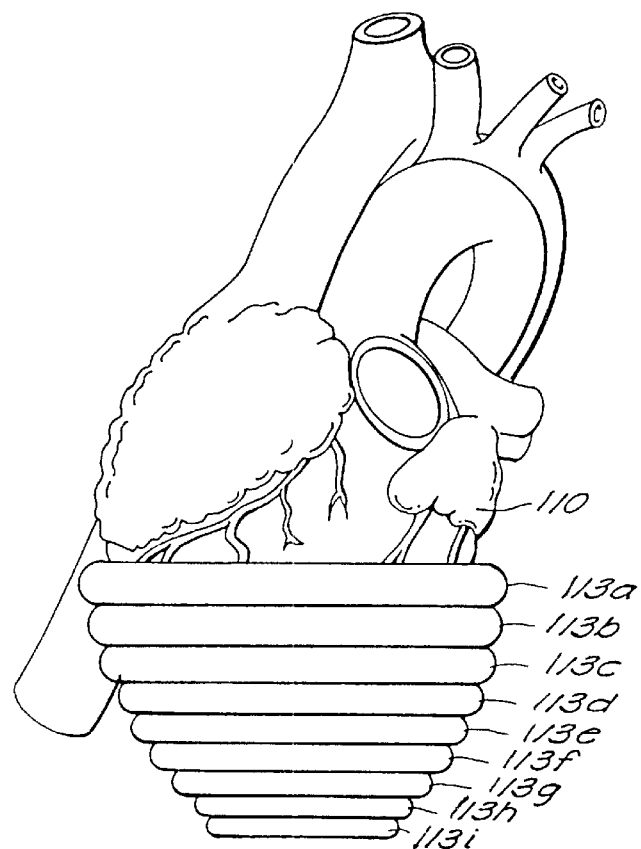
FIG. 20 is a perspective view of the heart girdle of FIGS. 19A and 19B showing the horizontal segments.
Figure 21:
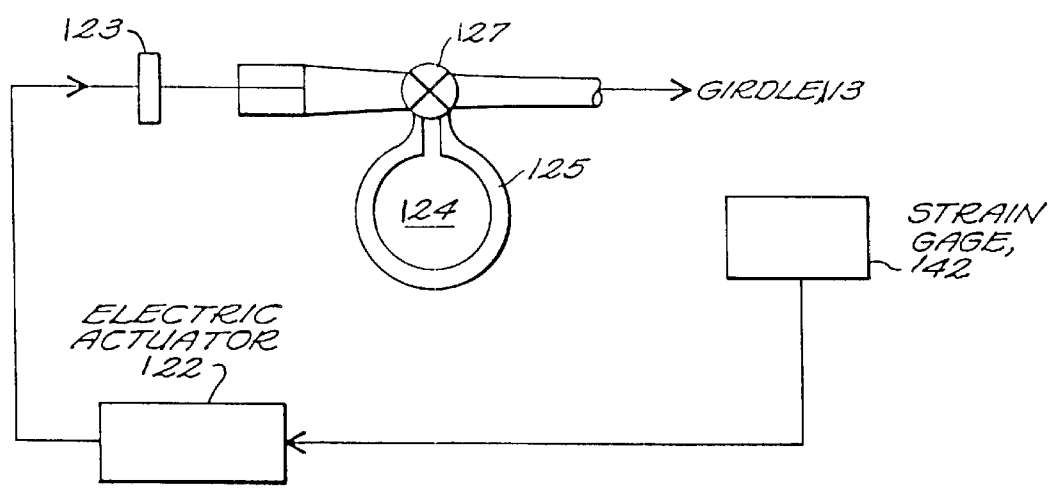
FIG. 21 is an illustration generally in block diagram form of a control system for the heart girdle of FIG. 19 including a strain gauge and electronic actuator to maintain constant tension at the interface between the girdle and the heart muscle.

In FIG. 19A, the natural heart 110 is shown with the left ventricle 112 somewhat dilated and with a girdle 117 surrounding both the left ventricle 112 and the right ventricle 111. The girdle 117 is formed as illustrated in FIG. 20, with a series of horizontal segments 113*a*–113*i* encircling the heart 110, the segments toward the apex of the heart being smaller in cross section and in length. The girdle segments 113 are filled with hydraulic fluid which is maintained at a constant volume during the beating of the heart. In this arrangement, the girdle is entirely passive and a distensible girdle lining 118 conforms to the shape of the heart at the myocardium girdle lining interface by virtue of the pressure of the fluid filled segments 113 against the distensible inner lining 118. As shown in FIG. 21, when the girdle is implanted around a natural heart, the volume is controlled through a three-way valve 127 which controls the amount of fluid supplied to the girdle segments 113 from reservoir 125, which is formed of a rigid casing 124.

In FIG. 21, a control system for controlling the fluid pressure in the segments 113 according to the tension in liner 118 is shown. The fluid pressure in girdle 113 is controlled by a feedback loop including a strain gauge 142 placed at the interface between the inner lining 118 and the myocardium providing a sensed value for the tension of the myocardium, to hydraulic actuating electronics 122 which may be a conventional hydraulic control circuit. The electronic actuator 122 controls a conventional mechanical fluid actuator 123 which provides for increase or decrease of fluid within the girdle 113. This actuator operates in conjunction with a three-way valve 127 and fluid reservoir 125. The change in volume effected by this feedback, is not intended to, nor does it operate in the time frame of the beating of the natural heart. It is meant to adjust the volume over a much longer time period, typically days, weeks or months.

Figure 22:
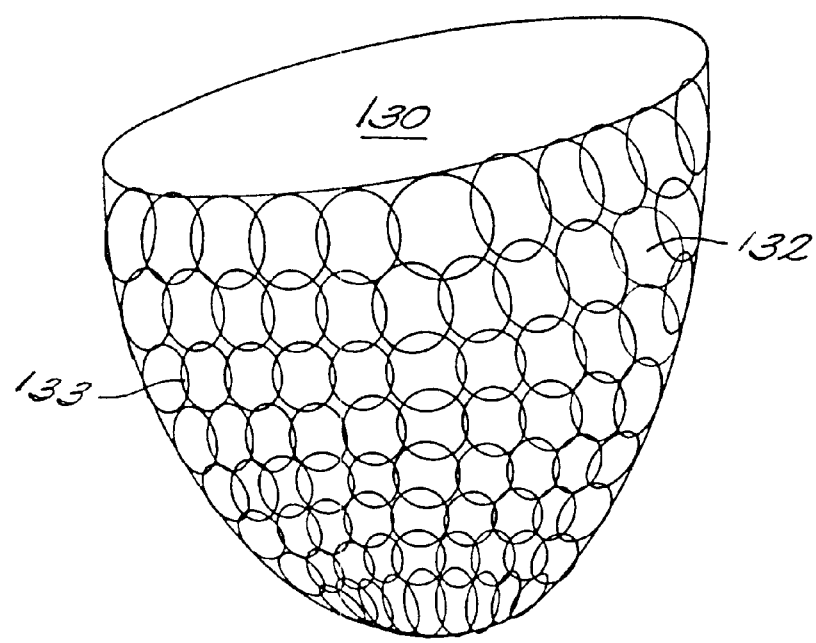
FIG. 22 is an illustration in perspective view of a heart girdle employing a flexible mesh of interlocked circular plastic loops.

In this configuration, the series of generally cylindrical segments 113 are typically formed of non distensible materials. They are attached to one another along the long axis of the cylinder and may be filled with fluid either individually or in parallel. When the fluid volume within the compartments 113 is very low, the girdle 113 assumes the shape shown in FIG. 19A providing for a larger diameter. On the other hand, when the fluid volume is increased the segments assume, at full inflation, a circular cross section thereby decreasing the inner perimeter very substantially, as illustrated in FIG. 19B. Thus, by controlling the volume of the fluids supplied to the individual segments 113, the inner diameter of the girdle 113 can be adjusted to be a close fit to the natural heart. This configuration has the advantage that, since there is no single vertical compartment, there is no gravity pooling of fluid in one portion of the girdle 113. FIG. 22 illustrates a second embodiment of this invention. The girdle 130 of FIG. 22 is an adjustable girdle made from a synthetic material that can limit tension, but is otherwise deformable to conform to the anatomical geometry of the heart. In this case, the girdle 130 is formed of a confining net 132 which is wrapped around the heart from the apex to the atrioventricular (A-V) groove. The purpose of this net is to limit the maximum diastolic dimension of the heart, while offering no resistance to systolic ejection. In the design illustrated in FIG. 22 a number of interlinked two-dimensional loops such as lightweight plastic rings 133 are interconnected to form the girdle or wrap 130. The loops 133 are free to move in all directions without restraint, since none are physically connected to each other. Rather, they are interlocked by having the loops or rings 133 pass through one another. The design of FIG. 22 presents no systolic load to the contracting heart. The loop-mesh 132 can readily conform to the shape of the heart with the change in surface area accompanying the heart contraction readily accommodated by the free loops.

Figure 23:
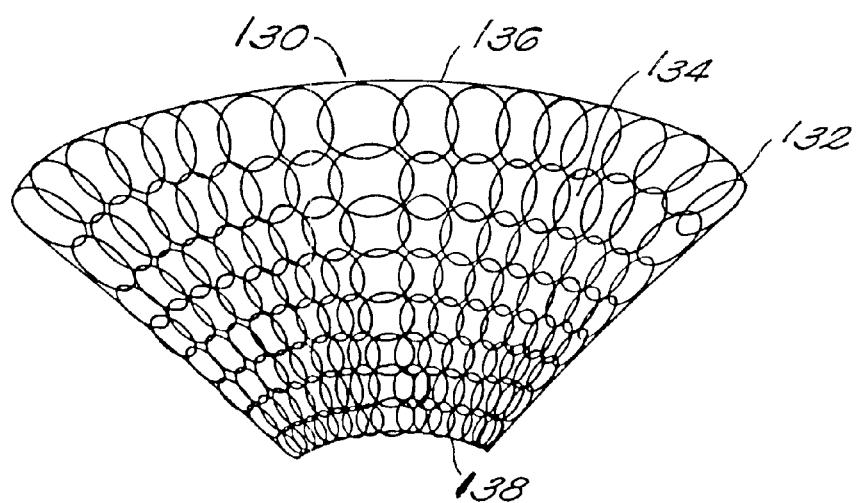
FIG. 23 is an illustration of a portion of a girdle constructed generally in accordance with the girdle construction of FIG. 22, but further including strings adapted to draw the girdle into decreasing diameter shape.
Figure 24:
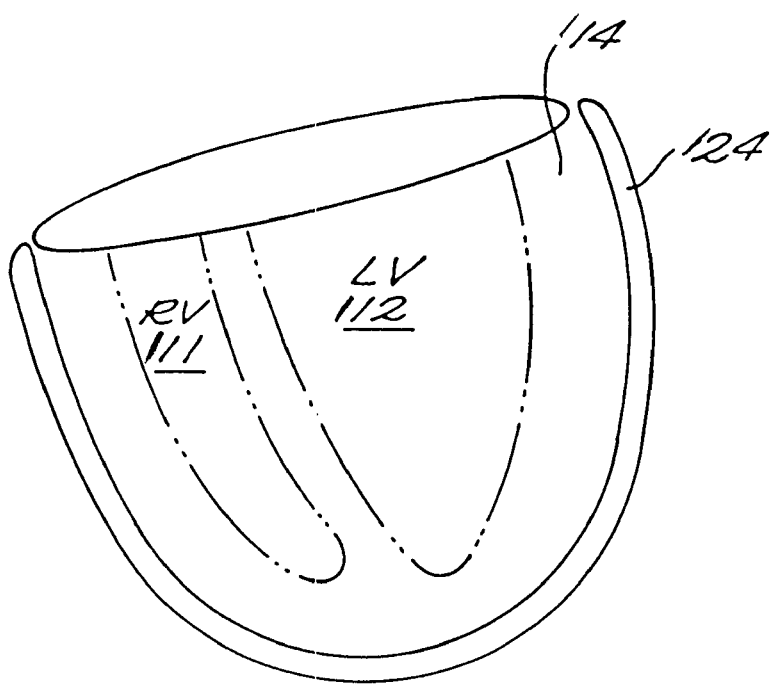
FIG. 24 is another embodiment of a portion of a passive girdle formed of a material characterized by a specific internal structure.

An alternative form of this loop-mesh girdle is shown in FIG. 23. In FIG. 23 a string system 134 is included with the string attached to the loops 133 to effect change in the size of the mesh by virtue of pulling the strings. This arrangement is able to accommodate a treatment modality for scheduled size reduction to the heart over a suitable period of time. In FIG. 23, a segment of the girdle or wrap 130 is shown. The original size of the wrap can be seen at the wide edge 136, while the narrowed down section is seen at the ridge 138 of the wrap. Pulling on the two ends of two sets of strings reduces the size of the mesh in two directions. This can be done during a thoracoscopy or through a cutaneous access port. In the construction illustrated in FIGS. 22 and 23 the net 130 will be attached at several attachment points, typically 4 to 6 in number, at the A-V groove and also perhaps near the apex of the natural heart. At the original implant the surgeon will optimize the fit to the heart as it is existing and will adjust the size through the mechanism described above. This design will accommodate spontaneous heart size reduction even though some parts of the mesh may adhere to the epicardium. However, due to relative motion between the loops, it is unlikely that the mesh will become fully encapsulated. In FIG. 24 there is shown a girdle in accordance with this invention which is formed of a sheet of an expanded polytetrafluroethylene (PTFE) material 124, prestressed such that it remains below its elastic limit and its tension in the plane of the sheet is sufficient to create radially inward forces, thus resisting expansion while permitting inward compression. In other words the girdle will resist further expansion while fittingly accommodating shrinkage. Other materials may be employed, provided that they exhibit the above elasticity characteristics.

Figure 25:
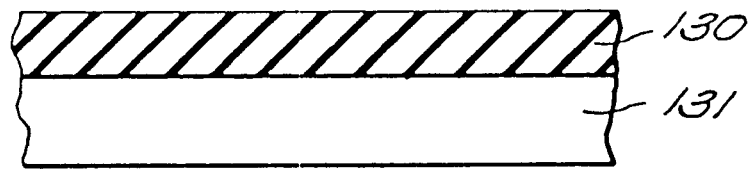
FIG. 25 is a cross sectional drawing of a girdle-myocardium interface constructed of biologically engineered myocardial tissue.

In FIG. 25 there is illustrated a cross sectional view of a tissue engineered girdle lining having a polymer scaffold 131 which has been seeded with myocardial cells harvested from the recipient mounted on a polymer substrate 131, the substrate either facing a girdle structure or forming the inner surface of that girdle. The tissue engineered lining faces the patient's myocardium. Such a lining reduces the irritation which may occur between the epicardium and artificial materials employed to form the girdle itself. The lining 130. would, over time, integrate biologically to the patient's myocardium.

Techniques for cell scaffold engineering are described in the literature. Two examples being, Biodegradable Polymer Scaffolds for Tissue Engineering by Lisa E. Freed, Gordana Vunjak-Novakovic, Robert J. Biron, Dana B. Eagles, Daniel C. Lesnoy, Sandra K. Barlow and Robert Langer and Tissue by Robert Langer and Joseph P. Vacanti, Biotechnology, Vol. 12, July 1994 and Tissue Engineering, Robert Langer and Joseph P. Vacanti, Science, Vol. 260 May 14, 1993.

These tissue engineering techniques may also be employed with respect to other artificial materials which come in contact with the heart in various surgical situations including the active devices described hereinabove and in U.S. patent application Ser. No. 08/490,080, filed Jun. 13, 1995.

Having described the above specific embodiments of this invention, other embodiments implementing the concepts of this invention will doubtless occur. While specific details of an artificial myocardium and artificial myocardium assist system have been illustrated, it will be understood that other embodiments,may be formed employing the principles of this invention.

What is claimed is:

1. A passive cardiac device, said device comprising:
   a biomedical material that is sized to be applied to a epicardial surface of the heart and which is passive and capable of expanding to a predetermined size after disposition about the heart, said predetermined size selected to constrain cardiac expansion beyond a predetermined limit.

2. The cardiac device according to claim 1 wherein said biomedical material is sized to locally constrain ventricular cardiac expansion.

3. The cardiac device according to claim 1 wherein said biomedical material is a jacket with said predetermined size selected for said jacket to surround the epicardial surface of the heart and circumferentially constrain cardiac expansion.

4. The cardiac device according to claim 3 further comprising at least one inflatable member for selectively adjusting said predetermined size of said jacket.

5. The cardiac device according to claim 4, wherein said at least one inflatable member is formed of an elongated segment having a longitudinal axis adapted to be substantially aligned with a major axis of the heart extending from the top of the heart to the apex.

6. The cardiac device according to claim 5, wherein said at least one inflatable member comprises a plurality of generally parallel elongated segments adapted to converge toward the apex.

7. The cardiac device according to claim 1 further comprising a mechanism for selectively adjusting said predetermined size.

8. The cardiac device of claim 7, wherein said mechanism comprises a lateral attachment device for circumferential adjustment of said cardiac device.

9. The cardiac device according to claim 1 wherein said biomedical material comprises an open mesh.

10. The cardiac device according to claim 1 wherein said biomedical material is a synthetic material that can limit tension but is otherwise deformable to conform to the anatomical geometry of the heart.

11. The cardiac device according to claim 1 wherein the biomedical material comprises a confining net structure that provides a sustained dimensional constraint on the heart.

12. The cardiac device according to claim 1 wherein the biomedical material comprises a mesh and the device further includes at least one adjustment string for adjusting the mesh to set a desired inner perimeter.

13. The cardiac device according to claim 1 wherein the biomedical material comprises an interlinked open loop mesh structure.

14. The cardiac device according to claim 1 wherein the biomedical material comprises a mesh which limits the maximum diastolic dimension of the heart without resistance to systolic ejection.

15. The cardiac device according to claim 1 wherein the biomedical material comprises a two-dimensional net formed by interconnected rings.

16. A passive cardiac device for constraining cardiac size during diastole, said device comprising:
   a biomedical material for contacting an epicardial surface of a patient's heart which is configured to circumferentially surround said epicardial surface of said patient's heart and is passive but capable of limited expansion;
   configured biomedical material having a base end and an apical end; and
   said configured biomedical material providing cardiac constraint beyond a defined limit after disposition about the heart during diastole without substantially assisting cardiac contraction during systole.

17. The cardiac device according to claim 16 wherein the biomedical material comprises a confining net structure that provides a sustained dimensional constraint on the heart.

18. The cardiac device according to claim 16 wherein the biomedical material comprises a mesh and the device further includes at least one adjustment string for adjusting the mesh to set a desired inner perimeter.

19. The cardiac device according to claim 16 wherein the biomedical material comprises an interlinked open loop mesh structure.

20. The cardiac device according to claim 16 wherein the biomedical material comprises a mesh which limits the maximum diastolic dimension of the heart without resistance to systolic ejection.

21. The cardiac device according to claim 16 wherein the biomedical material comprises a two-dimensional net formed by interconnected rings.

22. The cardiac device according to claim 16 wherein the biomedical material comprises a jacket with a predetermined size such that jacket can surround at least a portion of the epicardial surface of the heart and circumferentially constrain cardiac expansion.

23. The cardiac device according to claim 22 further comprising at least one inflatable member for selectively adjusting the predetermined size of the jacket.

24. The cardiac device according to claim 23 wherein the at least one inflatable member comprises an elongated segment having a longitudinal axis adapted to be substantially aligned with a major axis of the heart, the elongated segment extending from the top of the heart to the apex.

25. The cardiac device according to claim 23 wherein the at least one inflatable member comprises a plurality of elongate segments which converge towards the axis.

26. The cardiac device according to claim 23 wherein the device further comprises a mechanism for selectively adjusting said determined size.

27. The cardiac device according to claim 23 wherein the device further comprises at least one sensor for sensing tension in the jacket material.

28. The cardiac device according to claim 16 wherein the biomedical material further comprises a synthetic material that can limit tension but is otherwise deformable to conform to the anatomical geometry of the heart.

29. A method for cardiac treatment, said method comprising:
   selecting a cardiac device, said cardiac device being passive and comprising a biomedical material that is sized to be applied to the epicardial surface of a heart, said cardiac device expanding to a predetermined size after disposition about the heart, said predetermined size selected to constrain cardiac expansion beyond a predetermined limit;
   applying said cardiac device to the epicardial surface of the heart; and
   securing said cardiac device to said epicardial surface of the heart.

30. The method according to claim 29 wherein said cardiac device is further arranged to locally constrain said cardiac expansion.

31. The method according to claim 29 wherein said cardiac device comprises a jacket with said predetermined size selected for said jacket to surround the epicardial surface of the heart and circumferentially constrain cardiac expansion.

32. The method according to claim 29, further comprising the step of periodically adjusting said predetermined size as cardiac dilatation is reduced.

33. The method according to claim 29, wherein said cardiac device comprises a mechanism for selectively adjusting said predetermined size.

34. The method according to claim 33, wherein said mechanism comprises at least one inflatable member for selectively adjusting said predetermined size of said cardiac device.

35. The method according to claim 33, wherein said mechanism comprises a lateral attachment device for selective circumferential adjustment of said cardiac device.

36. The method according to claim 33, wherein said mechanism comprises at least one inflatable member for selectively periodically adjusting said predetermined size of said cardiac device.

37. The cardiac device of claim 33, wherein said mechanism comprises a lateral attachment device for selective, periodic circumferential adjustment of said cardiac device.

* * * * *

UNITED STATES PATENT AND TRADEMARK OFFICE
CERTIFICATE OF CORRECTION

PATENT NO.     : 6,508,756 B1
DATED          : January 21, 2003
INVENTOR(S)    : Robert T. Kung, David M. Lederman, and Meir Rosenberg It is certified that error appears in the above-identified patent and that said Letters Patent is hereby corrected as shown below:

<u>Title page,</u>
Item [56], FOREIGN PATENT DOCUMENTS, "GB 1009457" should read
-- SU 1009457 --; and "GB 1734767" should read -- SU 1734767 --.

<u>Drawings,</u>
Figure 5, "BLOOD STROKE VOLUMN" should read -- BLOOD STROKE VOLUME --;

<u>Column 9,</u>
Line 67, "volumne" should read -- volume --;

<u>Column 16,</u>
Line 7, "a i cm" should read -- a 1 cm --;
Line 38, "pericardiurn" should read -- pericardium --;
Line 42, "polyurethane" should read -- polyetherurethane --;

<u>Column 18,</u>
After line 48, insert missing paragraph:
    -- According to equation (1), it can be seen that an increase in mechanical work by a large factor results in a small increase in oxygen consumption, but an increase in tension time causes a large increase in oxygen consumption. Passive girdling of the heart, as illustrated in FIGS. 19-21, acts to limit or reduce the ventricular size of the diseased ventricle. Over an extended period of time, which may be days or weeks, the fluid 114 volume may be increased, thereby decreasing the periphery of the interface lining 118 of the girdle, which may over a period of time actually decrease the dilatation of the ventricle 112. --;

<u>Column 20,</u>
Lines 14-15, delete "and Tissue by Robert Langer and Joseph P. Vacanti";
Line 34, reads "surface of the heart" should read -- surface of a heart --;

UNITED STATES PATENT AND TRADEMARK OFFICE
CERTIFICATE OF CORRECTION

PATENT NO.    : 6,508,756 B1
DATED         : January 21, 2003
INVENTOR(S)   : Robert T. Kung, David M. Lederman, and Meir Rosenberg It is certified that error appears in the above-identified patent and that said Letters Patent is hereby corrected as shown below:

Column 22,
Line 6, reads "segments which converge" should read -- segments adapted to converge --;
Line 9, "said determined size" should read -- said predetermined size --.

Signed and Sealed this

Second Day of September, 2003

JAMES E. ROGAN
*Director of the United States Patent and Trademark Office*